United States Patent [19]

Talley et al.

[11] Patent Number: 5,434,178
[45] Date of Patent: Jul. 18, 1995

[54] 1,3,5 TRISUBSTITUTED PYRAZOLE COMPOUNDS FOR TREATMENT OF INFLAMMATION

[75] Inventors: John J. Talley; Donald J. Rogier, Jr., both of St. Louis, Mo.

[73] Assignee: G.D. Searle & Co., Skokie, Ill.

[21] Appl. No.: 160,517

[22] Filed: Nov. 30, 1993

[51] Int. Cl.⁶ .................. A61K 31/415; C07D 231/12; C07D 231/14
[52] U.S. Cl. ..................................... 514/406; 514/407; 548/370.7; 548/371.4; 548/374.1; 548/375.1; 548/377.1
[58] Field of Search ............... 548/370.7, 371.4, 374.1, 548/375.1, 377.1; 514/406, 407

[56] References Cited

U.S. PATENT DOCUMENTS

| | | | |
|---|---|---|---|
| 3,254,093 | 5/1966 | Huisgen et al. | 260/295 |
| 4,146,721 | 3/1979 | Rainer | 548/374 |
| 5,134,142 | 7/1992 | Matsuo et al. | 514/255 |

OTHER PUBLICATIONS

H. Faidallah et al., Pak. J. Sci. Ind. Res., 35, 213 (1992).
H. Mokhtar et al., Pak. J. Sci. Ind. Res., 35, 428 (1992).
H. Faid-Allah et al., Ind. J. Chem., 27B, 245 (1988).
R. Soliman et al., J. Pharm. Sci., 76, 626 (1987).
H. Faidallal et al., Pak. J. Sci. Ind. Res., 35, 8 (1992).
R. Soliman et al., J. Pharm. Sci., 70, 606 (1981).

*Primary Examiner*—Richard L. Raymond
*Attorney, Agent, or Firm*—Joseph W. Bulock; J. Timothy Keane

[57] ABSTRACT

A class of 1,3,5-triaryl or heteroaryl pyrazoles is described for the treatment of inflammation, including treatment of pain and disorders such as arthritis. Compounds of particular interest are of Formula I

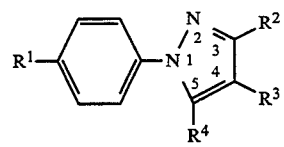

wherein $R^1$ is lower alkylsulfonyl or sulfamyl; wherein $R^2$ is aryl or heteroaryl; wherein $R^2$ is optionally substituted at substitutable positions with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; wherein $R^4$ is aryl or heteroaryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided $R^2$ and $R^4$ cannot be phenyl or substituted triazole, when $R^1$ is sulfamyl; further provided $R^2$ cannot be 4-methoxyphenyl or 4-methylphenyl when $R^4$ is 4-methoxyphenyl or 4-methylphenyl and when $R^1$ is sulfamyl; and further provided that $R^2$ cannot be tetrazole when $R^4$ is fluorophenyl, and when $R^1$ is methylsulfonyl; or a pharmaceutically-acceptable salt thereof.

29 Claims, No Drawings

1,3,5 TRISUBSTITUTED PYRAZOLE COMPOUNDS FOR TREATMENT OF INFLAMMATION

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Pyrazole compounds have been used in the treatment of inflammation. U.S. Pat. No. 5,134,142 to Matsuo et al describes 1,5-diaryl pyrazoles, and more particularly, 1-(4-fluorophenyl)-5-[4-(methylsulfonyl)phenyl]-3-(5-tetrazolyl)pyrazole, as having anti-inflammatory activity.

U.S. Pat. No. 4,146,721 to Rainer describes 1,3,5-triphenyl pyrazoles as useful analgesics, anti-inflammatory agents and antipyretics, and specifically describes 1,3,5-triphenyl-pyrazol-4-acetamide.

U.S. Pat. No. 3,254,093 to Huisgen et al describes a process for preparing pyrazoles, including ethyl-[1,3,5-triphenyl-1H-pyrazole-4-carboxylate.

The synthesis of a series of [3-phenyl-5-(2-phenyl-triazol-4-yl)]-1H-pyrazol-1-yl]benzenesulfonamides is described [H. Faidallah et al, *Pak. J. Sci. Ind. Res.*, 35, 213 (1992)], and specifically 4-[4-bromo-3-(4-methylphenyl)-5-(2-phenyl-2H-1,2,3-triazol-4-yl)-1H-pyrazol-1-yl]benzenesulfonamide. The synthesis of a series of related triazole substituted pyrazolyl benzenesulfonamides has been described [H. Mokhtar et al, *Pak. J. Sci. Ind. Res.*, 35, 428 (1992)].

The use of 4-[3-(4-aminophenyl)-5-phenyl-1H-pyrazol-1-yl]benzenesulfonamide as an intermediate in the synthesis of the corresponding benzenesulfonylureas has been described [H. Faid-Allah et al, *Ind. J. Chem.*, 27B, 245 (1988)]. An intermediate for antidiabetic agents, 4-[3-phenyl-5-bromophenyl-1H-pyrazol-1-yl]benzenesulfonamide, has been described [R. Soliman et al, *J. Pharm. Sci.*, 76, 626 (1987)]. The condensation of sulfamylphenylhydrazines with chalcones to produce 4-[3,5-diphenyl-pyrazol-1-yl]benzenesulfonamides has been reported, which are potential hypoglycemic agents [H. Faidallah et al, *Pak. J. Sci. Ind. Res.*, 35, 8 (1992)]. Specifically, 4-[3,5-bis(4-methoxyphenyl)-1H-pyrazol-1-yl]benzenesulfonamide is described. 4-[3,5-Diphenyl-1H-pyrazol-1-yl]benzenesulfonamide has been produced and evaluated for antidiabetic activity [R. Soliman et al, *J. Pharm. Sci.*, 70, 606 (1981)].

DESCRIPTION OF THE INVENTION

A class of compounds useful in the treatment of inflammation-related disorders is defined by Formula I:

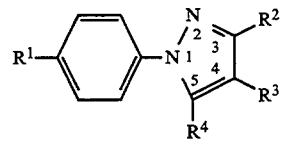

wherein $R^1$ is alkylsulfonyl or sulfamyl; wherein $R^2$ is aryl or heterocyclic; wherein $R^2$ is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino; wherein $R^3$ is selected from hydrido, alkyl, haloalkyl, cyano, carboxyl, alkoxycarbonyl, amino, acyl, acylamino, halo and alkylsulfonylamino; wherein $R^4$ is aryl or heterocyclic; wherein $R^4$ is optionally substituted at with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino; provided $R^2$ and $R^4$ cannot be phenyl or substituted triazole, when $R^1$ is sulfamyl; further provided $R^2$ cannot be 4-methoxyphenyl or 4-methylphenyl when $R^4$ is 4-methoxyphenyl or 4-methylphenyl and when $R^1$ is sulfamyl; and further provided that $R^2$ cannot be tetrazole when $R^4$ is fluorophenyl and when $R^1$ is methylsulfonyl; or a pharmaceutically-acceptable salt thereof.

The phrase "further provided", as used in the above description, is intended to mean that the denoted proviso is not to be considered conjunctive with any of the other provisos.

Compounds of Formula I would be useful for the treatment of inflammation in a subject, and for treatment of other inflammation-associated disorders, such as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, systemic lupus erythematosus, osteoarthritis and juvenile arthritis. Such compounds of Formula I would be useful in the treatment of asthma, bronchitis, menstrual cramps, tendinitis, bursiris, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis. Compounds of Formula I would be useful in treating inflammation in such diseases as vascular diseases, migraine headaches, periarteritis nodosa, thyroidiris, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. The compounds are useful as anti-inflammatory agents, such as for the treatment of arthritis, with the additional benefit of having significantly less harmful side effects.

A preferred class of compounds embraced by Formula I consists of those compounds wherein $R^1$ is lower alkylsulfonyl or sulfamyl; wherein $R^2$ is aryl or heteroaryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; wherein $R^4$ is aryl or heteroaryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided $R^2$ and $R^4$ cannot be phenyl or substituted triazole, when $R^1$ is sulfamyl; further provided $R^2$ cannot be 4-methoxyphenyl or 4-methylphenyl when $R^4$ is 4-methoxyphenyl or 4-methylphenyl and when $R^1$ is sulfamyl; and further provided that $R^2$ cannot be tetrazole when $R^4$ is fluorophenyl, and when $R^1$ is methylsulfonyl; or a pharmaceutically-acceptable salt thereof.

A more preferred class of compounds embraced by Formula I consists of those compounds wherein $R^1$ is lower alkylsulfonyl; wherein $R^2$ is aryl or heteroaryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; wherein $R^4$ is aryl or heteroaryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided that $R^2$ cannot be tetrazole when $R^4$ is fluorophenyl; or a pharmaceutically-acceptable salt thereof.

A class of compounds of particular interest consists of those compounds of Formula I wherein $R^1$ is methylsulfonyl; wherein $R^2$ is selected from phenyl, pyridyl, furyl, pyrryl, pyrimidyl, pyrazinyl, pyrazolyl, oxazolyl, isoxazolyl, imidazolyl, thiazolyl, pyranyl and thienyl; wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH-$; wherein $R^4$ is selected from phenyl, pyridyl, furyl, pyrryl, pyrimidyl, pyrazinyl, pyrazolyl, oxazolyl, isoxazolyl, imidazolyl, thiazolyl, pyranyl, and thienyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; or a pharmaceutically-acceptable salt thereof.

A family of specific compounds of particular interest within Formula I consists of compounds, and pharmaceutically-acceptable salts thereof, as follows:

1-(4-methylsulfonylphenyl)-3,5-(4-chlorophenyl)-pyrazole;

1-(4-methylsulfonylphenyl)-3-(3,5-difluorophenyl)-5-(4-chlorophenyl)pyrazole;

1-(4-methylsulfonylphenyl)-3-(2,5-difluorophenyl)-5-(4-chlorophenyl)pyrazole;

1-(4-methylsulfonylphenyl)-3-(3,4-difluorophenyl)-5-(4-chlorophenyl)pyrazole;

1-(4-methylsulfonylphenyl)-3-(4-methoxyphenyl)-5-(4-chlorophenyl)pyrazole;

1-(4-methylsulfonylphenyl)-3-(3-chlorophenyl)-5-(4-chlorophenyl)pyrazole;

1-(4-methylsulfonylphenyl)-3-(2,4,6-trifluorophenyl)-5-(4-chlorophenyl)pyrazole;

1-(4-methylsulfonylphenyl)-3-(3,4-dimethoxyphenyl)-5-(4-chlorophenyl)pyrazole;

1-(4-methylsulfonylphenyl)-3-(3,4-dichlorophenyl)-5-(4-chlorophenyl)pyrazole;

1-(4-methylsulfonylphenyl)-3-(2-chlorophenyl)-5-(4-chlorophenyl)pyrazole;

1-(4-methylsulfonylphenyl)-3-(2,4-dichlorophenyl)-5-(4-chlorophenyl)pyrazole;

1-(4-methylsulfonylphenyl)-3-(3,5-dichlorophenyl)-5-(4-chlorophenyl)pyrazole;

1-(4-methylsulfonylphenyl)-3-(2,4-dimethoxyphenyl)-5-(4-chlorophenyl)pyrazole;

1-(4-methylsulfonylphenyl)-3-(2,5-dichlorophenyl)-5-(4-chlorophenyl)pyrazole;

1-(4-methylsulfonylphenyl)-3-(4-methylphenyl)-5-(4-chlorophenyl)pyrazole;

1-(4-methylsulfonylphenyl)-3-(3-methylphenyl)-5-(4-chlorophenyl)pyrazole;

1-(4-methylsulfonylphenyl)-3-(2-methylphenyl)-5-(4-chlorophenyl)pyrazole;

1-(4-methylsulfonylphenyl)-3-(2,4-dimethylphenyl)-5-(4-chlorophenyl)pyrazole;
1-(4-methylsulfonylphenyl)-3-(2,4,6-trimethylphenyl)-5-(4-chlorophenyl)pyrazole;
1-(4-methylsulfonylphenyl)-3-(2,5-dimethylphenyl)-5-(4-chlorophenyl)pyrazole;
1-(4-methylsulfonylphenyl)-3-(3,5-dimethylphenyl)-5-(4-chlorophenyl)pyrazole;
1-(4-methylsulfonylphenyl)-3-(2,6-dimethylphenyl)-5-(4-chlorophenyl)pyrazole;
1-(4-methylsulfonylphenyl)-3-(4-nitrophenyl)-5-(4-chlorophenyl)pyrazole;
1-(4-methylsulfonylphenyl)-3-(3-nitrophenyl)-5-(4-chlorophenyl)pyrazole;
1-(4-methylsulfonylphenyl)-3-(2-nitrophenyl)-5-(4-chlorophenyl)pyrazole;
1-(4-methylsulfonylphenyl)-3-(4-methylthiophenyl)-5-(4-chlorophenyl)pyrazole;
1-(4-methylsulfonylphenyl)-3-(3-methylthiophenyl)-5-(4-chlorophenyl)pyrazole;
1-(4-methylsulfonylphenyl)-3-(2-methylthiophenyl)-5-(4-chlorophenyl)pyrazole;
1-(4-methylsulfonylphenyl)-3-(4-methoxy-2-fluorophenyl)-5-(4-chlorophenyl)pyrazole;
1-(4-methylsulfonylphenyl)-3-(2-methoxy-4-fluorophenyl)-5-4-chlorophenyl)pyrazole;
1-(4-methylsulfonylphenyl)-3-(4-aminophenyl)-5-(4-chlorophenyl)pyrazole;
1-(4-methylsulfonylphenyl)-3-(3-aminophenyl)-5-(4-chlorophenyl)pyrazole;
1-(4-methylsulfonylphenyl)-3-(2-aminophenyl)-5-(4-chlorophenyl)pyrazole;
1-(4-methylsulfonylphenyl)-3-(4-pyridyl)-5-chlorophenyl)pyrazole;
1-(4-methylsulfonylphenyl)-3-(3-pyridyl)-5-(4-chlorophenyl)pyrazole;
1-(4-methylsulfonylphenyl)-3-(2-pyridyl)-5-(4-chlorophenyl)pyrazole;
1-(4-methylsulfonylphenyl)-3-(2-thienyl)-5-(4-chlorophenyl)pyrazole;
1-(4-methylsulfonylphenyl)-3-(3-thienyl)-5-(4-chlorophenyl)pyrazole;
1-(4-methylsulfonylphenyl)-3-(2-furanyl)-5-(4-chlorophenyl)pyrazole;
1-(4-methylsulfonylphenyl)-3-(3-furanyl)-5-(4-chlorophenyl)pyrazole;
1-(4-methylsulfonylphenyl)-3-(4-trifluoromethylphenyl)-5-(4-chlorophenyl)pyrazole;
1-(4-methylsulfonylphenyl)-3-(3-trifluoromethylphenyl)-5-(4-chlorophenyl)pyrazole;
1-(4-methylsulfonylphenyl)-3-(2-trifluoromethylphenyl)-5-(4-chlorophenyl)pyrazole;
1-(4-methylsulfonylphenyl)-3-(4-hydroxyphenyl)-5-(4-chlorophenyl)pyrazole;
1-(4-methylsulfonylphenyl)-3-(3-hydroxyphenyl)-5-(4-chlorophenyl)pyrazole;
1-(4-methylsulfonylphenyl)-3-(2-hydroxyphenyl)-5-(4-chlorophenyl)pyrazole;
1-(4-methylsulfonylphenyl)-3-(4-carboxyphenyl)-5-(4-chlorophenyl)pyrazole;
1-(4-methylsulfonylphenyl)-3-(2-carboxyphenyl)-5-(4-chlorophenyl)pyrazole;
1-(4-methylsulfonylphenyl)-3-(3-carboxyphenyl)-5-(4-chlorophenyl)pyrazole;
1-(4-methylsulfonylphenyl)-3-(4-[N,N-dimethylamino]-phenyl)-5-(4-chlorophenyl)pyrazole;
1-(4-methylsulfonylphenyl)-3-(3-[N,N-dimethylamino]-phenyl)-5-(4-chlorophenyl)pyrazole;
1-(4-methylsulfonylphenyl)-3-(2-[N,N-dimethylamino]-phenyl)-5-(4-chlorophenyl)pyrazole;
1-(4-methylsulfonylphenyl)-3-(4-[N-methylamino]-phenyl)-5-(4-chlorophenyl)pyrazole;
1-(4-methylsulfonylphenyl)-3-(3-[N-methylamino]-phenyl)-5-(4-chlorophenyl)pyrazole;
1-(4-methylsulfonylphenyl)-3-(2-[N-methylamino]-phenyl)-5-(4-chlorophenyl)pyrazole;
1-(4-methylsulfonylphenyl)-3-(4-acetamidophenyl)-5-(4-chlorophenyl)pyrazole;
1-(4-methylsulfonylphenyl)-3-(3-acetamidophenyl)-5-(4-chlorophenyl)pyrazole;
1-(4-methylsulfonylphenyl)-3-(2-acetamidophenyl)-5-(4-chlorophenyl)pyrazole;
1-(4-methylsulfonylphenyl)-3-(4-cyanophenyl)-5-(4-chlorophenyl)pyrazole;
1-(4-methylsulfonylphenyl)-3-(3-cyanophenyl)-5-(4-chlorophenyl)pyrazole;
1-(4-methylsulfonylphenyl)-3-(2-cyanophenyl)-5-(4-chlorophenyl)pyrazole;
1-(4-methylsulfonylphenyl)-3-(2-bromophenyl)-5-(4-chlorophenyl)pyrazole;
1-(4-methylsulfonylphenyl)-3-(3-bromophenyl)-5-(4-chlorophenyl)pyrazole;
1-(4-methylsulfonylphenyl)-3-(4-bromophenyl)-5-(4-chlorophenyl)pyrazole;
1-(4-methylsulfonylphenyl)-3-(4-fluorophenyl)-5-(4-chlorophenyl)pyrazole;
1-(4-methylsulfonylphenyl)-3-(2,4-difluorophenyl)-5-(4-chlorophenyl)pyrazole;
1-(4-methylsulfonylphenyl)-3-(2,6-difluorophenyl)-5-(4-chlorophenyl)pyrazole;
1-(4-methylsulfonylphenyl)-3-(3-fluorophenyl)-5-(4-chlorophenyl)pyrazole;
1-(4-methylsulfonylphenyl)-3-phenyl-5-(4-chlorophenyl)pyrazole;
1-(4-methylsulfonylphenyl)-3-(4-chlorophenyl)-5-(phenyl)pyrazole;
1-(4-methylsulfonylphenyl)-3-(4-chlorophenyl)-5-(2-fluorophenyl)pyrazole;
1-(4-methylsulfonylphenyl)-3-(4-chlorophenyl)-5-(3-fluorophenyl)pyrazole;
1-(4-methylsulfonylphenyl)-3-(4-chlorophenyl)-5-(4-fluorophenyl)pyrazole;
1-(4-methylsulfonylphenyl)-3-(4-chlorophenyl)-5-(2,4-difluorophenyl)pyrazole;
1-(4-methylsulfonylphenyl)-3-(4-chlorophenyl)-5-(2,6-difluorophenyl)pyrazole;
1-(4-methylsulfonylphenyl)-3-(4-chlorophenyl)-5-(2,4,6-trifluorophenyl)pyrazole;
1-(4-methylsulfonylphenyl)-3-(4-chlorophenyl)-5-(3,4-difluorophenyl)pyrazole;
1-(4-methylsulfonylphenyl)-3-(4-chlorophenyl)-5-(2,5-difluorophenyl)pyrazole;
1-(4-methylsulfonylphenyl)-3-(4-chlorophenyl)-5-(2-chlorophenyl)pyrazole;
1-(4-methylsulfonylphenyl)-3-(4-chlorophenyl)-5-(3-chlorophenyl)pyrazole;
1-(4-methylsulfonylphenyl)-3-(4-chlorophenyl)-5-(4-chlorophenyl)pyrazole;
1-(4-methylsulfonylphenyl)-3-(4-chlorophenyl)-5-(2,4-dichlorophenyl)pyrazole;
1-(4-methylsulfonylphenyl)-3-(4-chlorophenyl)-5-(2,5-dichlorophenyl)pyrazole;
1-(4-methylsulfonylphenyl)-3-(4-chlorophenyl)-5-(2,6-dichlorophenyl)pyrazole;
1-(4-methylsulfonylphenyl)-3-(4-chlorophenyl)-5-(3,4-dichlorophenyl)pyrazole;

1-(4-methylsulfonylphenyl)-3-(4-chlorophenyl)-5-(2,4,6-trichlorophenyl)pyrazole;
1-(4-methylsulfonylphenyl)-3-(4-chlorophenyl)-5-(2-methylphenyl)pyrazole;
1-(4-methylsulfonylphenyl)-3-(4-chlorophenyl)-5-(3-methylphenyl)pyrazole;
1-(4-methylsulfonylphenyl)-3-(4-chlorophenyl)-5-(4-methylphenyl)pyrazole;
1-(4-methylsulfonylphenyl)-3-(4-chlorophenyl)-5-(2,4-dimethylphenyl)pyrazole;
1-(4-methylsulfonylphenyl)-3-(4-chlorophenyl)-5-(4-[N-methylamino]phenyl)pyrazole;
1-(4-methylsulfonylphenyl)-3-(4-chlorophenyl)-5-(2-[N-methylamino]phenyl)pyrazole;
1-(4-methylsulfonylphenyl)-3-(4-chlorophenyl)-5-(3-[N-methylamino]phenyl)pyrazole;
1-(4-methylsulfonylphenyl)-3-(4-chlorophenyl)-5-(3,4-difluorophenyl)pyrazole;
1-(4-methylsulfonylphenyl)-3-(4-chlorophenyl)-5-(2,5-dimethylphenyl)pyrazole;
1-(4-methylsulfonylphenyl)-3-(4-chlorophenyl)-5-(2,6-dimethylphenyl)pyrazole;
1-(4-methylsulfonylphenyl)-3-(4-chlorophenyl)-5-(3,4-dimethylphenyl)pyrazole;
1-(4-methylsulfonylphenyl)-3-(4-chlorophenyl)-5-(2,4,6-trimethylphenyl)pyrazole;
1-(4-methylsulfonylphenyl)-3-(4-chlorophenyl)-5-(2-methoxyphenyl)pyrazole;
1-(4-methylsulfonylphenyl)-3-(4-chlorophenyl)-5-(3-methoxyphenyl)pyrazole;
1-(4-methylsulfonylphenyl)-3-(4-chlorophenyl)-5-(4-methoxyphenyl)pyrazole;
1-(4-methylsulfonylphenyl)-3-(4-chlorophenyl)-5-(2,4-dimethoxyphenyl)pyrazole;
1-(4-methylsulfonylphenyl)-3-(4-chlorophenyl)-5-(2,5-dimethoxyphenyl)pyrazole;
1-(4-methylsulfonylphenyl)-3-(4-chlorophenyl)-5-(2,6-dimethoxyphenyl)pyrazole;
1-(4-methylsulfonylphenyl)-3-(4-chlorophenyl)-5-(3,4-dimethoxyphenyl)pyrazole;
1-(4-methylsulfonylphenyl)-3-(4-chlorophenyl)-5-(2-trifluoromethylphenyl)pyrazole;
1-(4-methylsulfonylphenyl)-3-(4-chlorophenyl)-5-(3-trifluoromethylphenyl)pyrazole;
1-(4-methylsulfonylphenyl)-3-(4-chlorophenyl)-5-(4-trifluoromethylphenyl)pyrazole;
1-(4-methylsulfonylphenyl)-3-(4-chlorophenyl)-5-(2-aminophenyl)pyrazole;
1-(4-methylsulfonylphenyl)-3-(4-chlorophenyl)-5-(3-aminophenyl)pyrazole;
1-(4-methylsulfonylphenyl)-3-(4-chlorophenyl)-5-(4-aminophenyl)pyrazole;
1-(4-methylsulfonylphenyl)-3-(4-chlorophenyl)-5-(2-[N,N-dimethylamino]phenyl)pyrazole;
1-(4-methylsulfonylphenyl)-3-(4-chlorophenyl)-5-(3-[N,N-dimethylamino]phenyl)pyrazole;
1-(4-methylsulfonylphenyl)-3-(4-chlorophenyl)-5-(4-[N,N-dimethylamino]phenyl)pyrazole;
1-(4-methylsulfonylphenyl)-3-(4-chlorophenyl)-5-(4-methoxycarbonylphenyl)pyrazole;
1-(4-methylsulfonylphenyl)-3-(4-chlorophenyl)-5-(2-methoxycarbonylphenyl)pyrazole;
1-(4-methylsulfonylphenyl)-3-(4-chlorophenyl)-5-(2-nitrophenyl)pyrazole;
1-(4-methylsulfonylphenyl)-3-(4-chlorophenyl)-5-(3-nitrophenyl)pyrazole;
1-(4-methylsulfonylphenyl)-3-(4-chlorophenyl)-5-(4-nitrophenyl)pyrazole;
1-(4-methylsulfonylphenyl)-3-(4-chlorophenyl)-5-(2-methylthiophenyl)pyrazole;
1-(4-methylsulfonylphenyl)-3-(4-chlorophenyl)-5-(3-methylthiophenyl)pyrazole;
1-(4-methylsulfonylphenyl)-3-(4-chlorophenyl)-5-(4-methylthiophenyl)pyrazole;
1-(4-methylsulfonylphenyl)-3-(4-chlorophenyl)-5-(2-cyanophenyl)pyrazole;
1-(4-methylsulfonylphenyl)-3-(4-chlorophenyl)-5-(3-cyanophenyl)pyrazole;
1-(4-methylsulfonylphenyl)-3-(4-chlorophenyl)-5-(4-cyanophenyl)pyrazole;
1-(4-methylsulfonylphenyl)-3-(4-chlorophenyl)-5-(2-thienyl)pyrazole;
1-(4-methylsulfonylphenyl)-3-(4-chlorophenyl)-5-(3-thienyl)pyrazole;
1-(4-methylsulfonylphenyl)-3-(4-chlorophenyl)-5-(2-pyridyl)pyrazole;
1-(4-methylsulfonylphenyl)-3-(4-chlorophenyl)-5-(3-pyridyl)pyrazole;
1-(4-methylsulfonylphenyl)-3-(4-chlorophenyl)-5-(4-pyridyl)pyrazole;
1-(4-methylsulfonylphenyl)-3-(4-chlorophenyl)-5-(2-furanyl)pyrazole;
1-(4-methylsulfonylphenyl)-3-(4-chlorophenyl)-5-(3-furanyl)pyrazole;
1-(4-methylsulfonylphenyl)-3-(4-chlorophenyl)-5-(2-hydroxyphenyl)pyrazole;
1-(4-methylsulfonylphenyl)-3-(4-chlorophenyl)-5-(3-hydroxyphenyl)pyrazole;
1-(4-methylsulfonylphenyl)-3-(4-chlorophenyl)-5-(4-hydroxyphenyl)pyrazole;
1-(4-methylsulfonylphenyl)-3-(4-chlorophenyl)-5-(2-carboxyphenyl)pyrazole;
1-(4-methylsulfonylphenyl)-3-(4-chlorophenyl)-5-(3-carboxyphenyl)pyrazole;
1-(4-methylsulfonylphenyl)-3-(4-chlorophenyl)-5-(4-carboxyphenyl)pyrazole;
1-(4-methylsulfonylphenyl)-3-(4-chlorophenyl)-5-(2-methoxycarbonylphenyl)pyrazole;
1-(4-methylsulfonylphenyl)-3-(4-chlorophenyl)-5-(3-methoxycarbonylphenyl)pyrazole;
1-(4-methylsulfonylphenyl)-3-(4-chlorophenyl)-5-(3-ethoxycarbonylphenyl)pyrazole;
1-(4-methylsulfonylphenyl)-3-(4-chlorophenyl)-5-(4-ethoxycarbonylphenyl)pyrazole;
1-(4-methylsulfonylphenyl)-3-(4-chlorophenyl)-5-(2-acetamidophenyl)pyrazole;
1-(4-methylsulfonylphenyl)-3-(4-chlorophenyl)-5-(3-acetamidophenyl)pyrazole;
1-(4-methylsulfonylphenyl)-3-(4-chlorophenyl)-5-(4-acetamidophenyl)pyrazole;
1-(4-methylsulfonylphenyl)-3-(4-chlorophenyl)-5-(2-bromophenyl)pyrazole;
1-(4-methylsulfonylphenyl)-3-(4-chlorophenyl)-5-(3-bromophenyl)pyrazole;
1-(4-methylsulfonylphenyl)-3-(4-chlorophenyl)-5-(4-bromophenyl)pyrazole;
1-(4-methylsulfonylphenyl)-3,5-bis(4-methoxyphenyl)pyrazole;
1-(4-methylsulfonylphenyl)-3,5-bis(4-methylphenyl)pyrazole;
1-(4-methylsulfonylphenyl)-3,5-bis(4-nitrophenyl)pyrazole;
1-(4-methylsulfonylphenyl)-3,5-bis(4-methylthiophenyl)pyrazole;
1-(4-methylsulfonylphenyl)-3,5-bis(4-aminophenyl)pyrazole;

1-(4-methylsulfonylphenyl)-3,5-bis(4-trifluoromethylphenyl)pyrazole;
1-(4-methylsulfonylphenyl)-3,5-bis(4-hydroxyphenyl)-pyrazole;
1-(4-methylsulfonylphenyl)-3,5-bis(4-carboxyphenyl)-pyrazole;
1-(4-methylsulfonylphenyl)-3,5-bis(4-cyanophenyl)-pyrazole;
1-(4-methylsulfonylphenyl)-3,5-bis(4-bromophenyl)-pyrazole;
1-(4-methylsulfonylphenyl)-3,5-bis(4-fluorophenyl)-pyrazole;
1-(4-methylsulfonylphenyl)-3,5-bis(4-chlorophenyl)-4-methyl-pyrazole;
1-(4-methylsulfonylphenyl)-3,5-bis(4-chlorophenyl)-4-ethyl-pyrazole;
1-(4-methylsulfonylphenyl)-3,5-bis(4-chlorophenyl)-4-propyl-pyrazole;
1-(4-methylsulfonylphenyl)-3,5-bis(4-chlorophenyl)-4-butyl-pyrazole;
1-(4-methylsulfonylphenyl)-3,5-bis(4-chlorophenyl)-4-isopropyl-pyrazole;
1-(4-methylsulfonylphenyl)-3,5-bis(4-chlorophenyl)-4-trifluoromethyl-pyrazole;
1-(4-methylsulfonylphenyl)-3,5-bis(4-chlorophenyl)-4-cyano-pyrazole;
1-(4-methylsulfonylphenyl)-3,5-bis(4-chlorophenyl)-4-difluoromethyl-pyrazole;
1-(4-methylsulfonylphenyl)-3,5-bis(4-chlorophenyl)-4-carboxy-pyrazole;
1-(4-methylsulfonylphenyl)-3,5-bis(4-chlorophenyl)-4-methoxycarbonyl-pyrazole;
1-(4-methylsulfonylphenyl)-3,5-bis(4-chlorophenyl)-4-ethoxycarbonyl-pyrazole;
1-(4-methylsulfonylphenyl)-3,5-bis(4-chlorophenyl)-4-acetyl-pyrazole;
1-(4-methylsulfonylphenyl)-3,5-bis(4-chlorophenyl)-4-formyl-pyrazole;
1-(4-methylsulfonylphenyl)-3,5-bis(4-chlorophenyl)-4-amino-pyrazole;
1-(4-methylsulfonylphenyl)-3,5-bis(4-chlorophenyl)-4-acetamido-pyrazole;
1-(4-methylsulfonylphenyl)-3,5-bis(4-chlorophenyl)-4-(N-[methylsulfonyl])amino-pyrazole;
1-(4-methylsulfonylphenyl)-3,5-bis(4-chlorophenyl)-4-fluoro-pyrazole;
1-(4-methylsulfonylphenyl)-3,5-bis(4-chlorophenyl)-4-chloro-pyrazole; and
1-(4-methylsulfonylphenyl)-3,5-bis(4-chlorophenyl)-4-bromo-pyrazole.

A second more preferred class of compounds consists of those compounds of Formula I wherein $R^1$ is sulfamyl; wherein $R^2$ is aryl or heteroaryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; wherein $R^4$ is aryl or heteroaryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided $R^2$ and $R^4$ cannot be phenyl or substituted triazole; and further provided $R^2$ cannot be 4-methoxyphenyl or 4-methylphenyl when $R^4$ is 4-methoxyphenyl or 4-methylphenyl; or a pharmaceutically-acceptable salt thereof.

A second class of compounds of particular interest consists of those compounds of Formula I wherein $R^2$ is selected from phenyl, pyrryl, furyl, pyridyl, pyrimidyl, pyrazinyl, pyrazolyl, oxazolyl, isoxazolyl, imidazolyl, thiazolyl, pyranyl and thienyl; wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH-$; wherein $R^4$ is selected from phenyl, pyrryl, furyl, pyridyl, pyrimidyl, pyrazinyl, pyrazolyl, oxazolyl, isoxazolyl, imidazolyl, thiazolyl, pyranyl and thienyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; provided $R^2$ and $R^4$ cannot be phenyl; and further provided $R^2$ cannot be 4-methoxyphenyl or 4-methylphenyl when $R^4$ is 4-methoxyphenyl or 4-methylphenyl; or a pharmaceutically-acceptable salt thereof.

A second family of specific compounds of particular interest within Formula I consists of compounds, and pharmaceutically-acceptable salts thereof, as follows:
4-[3,5-bis(4-chlorophenyl)-1H-pyrazol-1-yl]benzenesulfonamide;
4-[3-(3,5-difluorophenyl)-5-(4-chlorophenyl)-1H-pyrazol-1-yl]benzenesulfonamide;

4-[3-(2,5-difluorophenyl)-5-(4-chlorophenyl)-1H-pyrazol-1-yl]benzenesulfonamide;
4-[3-(3,4-difluorophenyl)-5-(4-chlorophenyl)-1H-pyrazol-1-yl]benzenesulfonamide;
4-[3-(4-methoxyphenyl)-5-(4-chlorophenyl)-1H-pyrazol-1-yl]benzenesulfonamide;
4-[3-(3-chlorophenyl)-5-(4-chlorophenyl)-1H-pyrazol-1-yl]benzenesulfonamide;
4-[3-(2,4,6-trifluorophenyl)-5-(4-chlorophenyl)-1H-pyrazol-1-yl]benzenesulfonamide;
4-[3-(3,4-dimethoxyphenyl)-5-(4-chlorophenyl)-1H-pyrazol-1-yl]benzenesulfonamide;
4-[3-(3,4-dichlorophenyl)-5-(4-chlorophenyl)-1H-pyrazol-1-yl]benzenesulfonamide;
4-[3-(2-chlorophenyl)-5-(4-chlorophenyl)-1H-pyrazol-1-yl]benzenesulfonamide;
4-[3-(2,4-dichlorophenyl)-5-(4-chlorophenyl)-1H-pyrazol-1-yl]benzenesulfonamide;
4-[3-(3,4-dichlorophenyl)-5-(4-chlorophenyl)-1H-pyrazol-1-yl]benzenesulfonamide;
4-[3-(2,4-dimethoxyphenyl)-5-(4-chlorophenyl)-1H-pyrazol-1-yl]benzenesulfonamide;
4-[3-(2,5-dichlorophenyl)-5-(4-chlorophenyl)-1H-pyrazol-1-yl]benzenesulfonamide;
4-[3-(4-methylphenyl)-5-(4-chlorophenyl)-1H-pyrazol-1-yl]benzenesulfonamide;
4-[3-(3-methylphenyl)-5-(4-chlorophenyl)-1H-pyrazol-1-yl]benzenesulfonamide;
4-[3-(2-methylphenyl)-5-(4-chlorophenyl)-1H-pyrazol-1-yl]benzenesulfonamide;
4-[3-(2,4-dimethylphenyl)-5-(4-chlorophenyl)-1H-pyrazol-1-yl]benzenesulfonamide;
4-[3-(2,4,6-trimethylphenyl)-5-(4-chlorophenyl)-1H-pyrazol-1-yl]benzenesulfonamide;
4-[3-(2,5-dimethylphenyl)-5-(4-chlorophenyl)-1H-pyrazol-1-yl]benzenesulfonamide;
4-[3-(3,5-dimethylphenyl)-5-(4-chlorophenyl)-1H-pyrazol-1-yl]benzenesulfonamide;
4-[3-(2,6-dimethylphenyl)-5-(4-chlorophenyl)-1H-pyrazol-1-yl]benzenesulfonamide;
4-[3-(4-nitrophenyl)-5-(4-chlorophenyl)-1H-pyrazol-1-yl]benzenesulfonamide;
4-[3-(3-nitrophenyl)-5-(4-chlorophenyl)-1H-pyrazol-1-yl]benzenesulfonamide;
4-[3-(2-nitrophenyl)-5-(4-chlorophenyl)-1H-pyrazol-1-yl]benzenesulfonamide;
4-[3-(4-methylthiophenyl)-5-(4-chlorophenyl)-1H-pyrazol-1-yl]benzenesulfonamide;
4-[3-(3-methylthiophenyl)-5-(4-chlorophenyl)-1H-pyrazol-1-yl]benzenesulfonamide;
4-[3-(2-methylthiophenyl)-5-(4-chlorophenyl)-1H-pyrazol-1-yl]benzenesulfonamide;
4-[3-(4-methoxy-2-fluorophenyl)-5-(4-chlorophenyl)-1H-pyrazol-1-yl]benzenesulfonamide;
4-[3-(2-methoxy-4-fluorophenyl)-5-(4-chlorophenyl)-1H-pyrazol-1-yl]benzenesulfonamide;
4-[3-(4-aminophenyl)-5-(4-chlorophenyl)-1H-pyrazol-1-yl]benzenesulfonamide;
4-[3-(3-aminophenyl)-5-(4-chlorophenyl)-1H-pyrazol-1-yl]benzenesulfonamide;
4-[3-(2-aminophenyl)-5-(4-chlorophenyl)-1H-pyrazol-1-yl]benzenesulfonamide;
4-[3-(4-pyridyl)-5-(4-chlorophenyl)-1H-pyrazol-1-yl]benzenesulfonamide;
4-[3-(3-pyridyl)-5-(4-chlorophenyl)-1H-pyrazol-1-yl]benzenesulfonamide;
4-[3-(2-pyridyl)-5-(4-chlorophenyl)-1H-pyrazol-1-yl]benzenesulfonamide;
4-[3-(2-thienyl)-5-(4-chlorophenyl)-1H-pyrazol-1-yl]benzenesulfonamide;
4-[3-(3-thienyl)-5-(4-chlorophenyl)-1H-pyrazol-1-yl]benzenesulfonamide;
4-[3-(2-furanyl)-5-(4-chlorophenyl)-1H-pyrazol-1-yl]benzenesulfonamide;
4-[3-(3-furanyl)-5-(4-chlorophenyl)-1H-pyrazol-1-yl]benzenesulfonamide;
4-[3-(4-trifluoromethylphenyl)-5-(4-chlorophenyl)-1H-pyrazol-1yl]benzenesulfonamide;
4-[3-(3-trifluoromethylphenyl)-5-(4-chlorophenyl)-1H-pyrazol-1-yl]benzenesulfonamide;
4-[3-(2-trifluoromethylphenyl)-5-(4-chlorophenyl)-1H-pyrazol-1-yl]benzenesulfonamide;
4-[3-(4-hydroxyphenyl)-5-(4-chlorophenyl)-1H-pyrazol-1-yl]benzenesulfonamide;
4-[3-(3-hydroxyphenyl)-5-(4-chlorophenyl)-1H-pyrazol-1-yl]benzenesulfonamide;
4-[3-(2-hydroxyphenyl)-5-(4-chlorophenyl)-1H-pyrazol-1-yl]benzenesulfonamide;
4-[3-(4-carboxyphenyl)-5-(4-chlorophenyl)-1H-pyrazol-1-yl]benzenesulfonamide;
4-[3-(2-carboxyphenyl)-5-(4-chlorophenyl)-1H-pyrazol-1-yl]benzenesulfonamide;
4-[3-(3-carboxyphenyl)-5-(4-chlorophenyl)-1H-pyrazol-1-yl]benzenesulfonamide;
4-[3-(4-[N,N-dimethylamino]phenyl)-5-(4-chlorophenyl)-1H-pyrazol-1-yl]benzenesulfonamide;
4-[3-(3-[N,N-dimethylamino]phenyl)-5-(4-chlorophenyl)-1H-pyrazol-1-yl]benzenesulfonamide;
4-[3-(2-[N,N-dimethylamino]phenyl)-5-(4-chlorophenyl)-1H-pyrazol-1-yl]benzenesulfonamide;
4-[3-(4-[N-methylamino]phenyl)-5-(4-chlorophenyl)-1H-pyrazol-1-yl]benzenesulfonamide;
4-[3-(3-[N-methylamino]phenyl)-5-(4-chlorophenyl)-1H-pyrazol-1-yl]benzenesulfonamide;
4-[3-(2-[N-methylamino]phenyl)-5-(4-chlorophenyl)-1H-pyrazol-1-yl]benzenesulfonamide;
4-[3-(4-acetamidophenyl)-5-(4-chlorophenyl)-1H-pyrazol-1-yl]benzenesulfonamide;
4-[3-(3-acetamidophenyl)-5-(4-chlorophenyl)-1H-pyrazol-1-yl]benzenesulfonamide;
4-[3-(2-acetamidophenyl)-5-(4-chlorophenyl)-1H-pyrazol-1-yl]benzenesulfonamide;
4-[3-(4-cyanophenyl)-5-(4-chlorophenyl)-1H-pyrazol-1-yl]benzenesulfonamide;
4-[3-(3-cyanophenyl)-5-(4-chlorophenyl)-1H-pyrazol-1-yl]benzenesulfonamide;
4-[3-(2-cyanophenyl)-5-(4-chlorophenyl)-1H-pyrazol-1-yl]benzenesulfonamide;
4-[3-(2-bromophenyl)-5-(4-chlorophenyl)-1H-pyrazol-1-yl]benzenesulfonamide;
4-[3-(3-bromophenyl)-5-(4-chlorophenyl)-1H-pyrazol-1-yl]benzenesulfonamide;
4-[3-(4-bromophenyl)-5-(4-chlorophenyl)-1H-pyrazol-1-yl]benzenesulfonamide;
4-[3-(4-fluorophenyl)-5-(4-chlorophenyl)-1H-pyrazol-1-yl]benzenesulfonamide;
4-[3-(2,4-difluorophenyl)-5-(4-chlorophenyl)-1H-pyrazol-1-yl]benzenesulfonamide;
4-[3-(2,6-difluorophenyl)-5-(4-chlorophenyl)-1H-pyrazol-1-yl]benzenesulfonamide;
4-[3-(3-fluorophenyl)-5-(4-chlorophenyl)-1H-pyrazol-1-yl]benzenesulfonamide;
4-[3-(4-chlorophenyl)-5-(2-fluorophenyl)-1H-pyrazol-1-yl]benzenesulfonamide;
4-[3-(4-chlorophenyl)-5-(3-fluorophenyl)-1H-pyrazol-1-yl]benzenesulfonamide;

4-[3-(4-chlorophenyl)-5-(4-fluorophenyl)-1H-pyrazol-1-yl]benzenesulfonamide;
4-[3-(4-chlorophenyl)-5-(2,4-difluorophenyl)-1H-pyrazol-1-yl]benzenesulfonamide;
4-[3-(4-chlorophenyl)-5-(2,6-difluorophenyl)-1H-pyrazol-1-yl]benzenesulfonamide;
4-[3-(4-chlorophenyl)-5-(2,4,6-trifluorophenyl)-1H-pyrazol-1-yl]benzenesulfonamide;
4-[3-(4-chlorophenyl)-5-(3,4-difluorophenyl)-1H-pyrazol-1-yl]benzenesulfonamide;
4-[3-(4-chlorophenyl)-5-(2,5-difluorophenyl)-1H-pyrazol-1-yl]benzenesulfonamide;
4-[3-(4-chlorophenyl)-5-(2-chlorophenyl)-1H-pyrazol-1-yl]benzenesulfonamide;
4-[3-(4-chlorophenyl)-5-(3-chlorophenyl)-1H-pyrazol-1-yl]benzenesulfonamide;
4-[3-(4-chlorophenyl)-5-(2,4-dichlorophenyl)-1H-pyrazol-1-yl]benzenesulfonamide;
4-[3-(4-chlorophenyl)-5-(2,5-dichlorophenyl)-1H-pyrazol-1-yl]benzenesulfonamide;
4-[3-(4-chlorophenyl)-5-(2,6-dichlorophenyl)-1H-pyrazol-1-yl]benzenesulfonamide;
4-[3-(4-chlorophenyl)-5-(3,4-dichlorophenyl)-1H-pyrazol-1-yl]benzenesulfonamide;
4-[3-(4-chlorophenyl)-5-(2,4,6-trichlorophenyl)-1H-pyrazol-1-yl]benzenesulfonamide;
4-[3-(4-chlorophenyl)-5-(2-methylphenyl)-1H-pyrazol-1-yl]benzenesulfonamide;
4-[3-(4-chlorophenyl)-5-(3-methylphenyl)-1H-pyrazol-1-yl]benzenesulfonamide;
4-[3-(4-chlorophenyl)-5-(4-methylphenyl)-1H-pyrazol-1-yl]benzenesulfonamide;
4-[3-(4-chlorophenyl)-5-(2,4-dimethylphenyl)-1H-pyrazol-1-yl]benzenesulfonamide;
4-[3-(4-chlorophenyl)-5-(4-[N-methylamino]phenyl)-1H-pyrazol-1-yl]benzenesulfonamide;
4-[3-(4-chlorophenyl)-5-(2-[N-methylamino]phenyl)-1H-pyrazol-1-yl]benzenesulfonamide;
4-[3-(4-chlorophenyl)-5-(3-[N-methylamino]phenyl)-1H-pyrazol-1-yl]benzenesulfonamide;
4-[3-(4-chlorophenyl)-5-(3,4-difluorophenyl)-1H-pyrazol-1-yl]benzenesulfonamide;
4-[3-(4-chlorophenyl)-5-(2,5-dimethylphenyl)-1H-pyrazol-1-yl]benzenesulfonamide;
4-[3-(4-chlorophenyl)-5-(2,6-dimethylphenyl)-1H-pyrazol-1-yl]benzenesulfonamide;
4-[3-(4-chlorophenyl)-5-(3,4-dimethylphenyl)-1H-pyrazol-1-yl]benzenesulfonamide;
4-[3-(4-chlorophenyl)-5-(2,4,6-trimethylphenyl)-1H-pyrazol-1-yl]benzenesulfonamide;
4-[3-(4-chlorophenyl)-5-(2-methoxyphenyl)-1H-pyrazol-1-yl]benzenesulfonamide;
4-[3-(4-chlorophenyl)-5-(3-methoxyphenyl)-1H-pyrazol-1-yl]benzenesulfonamide;
4-[3-(4-chlorophenyl)-5-(4-methoxyphenyl)-1H-pyrazol-1-yl]benzenesulfonamide;
4-[3-(4-chlorophenyl)-5-(2,4-dimethoxyphenyl)-1H-pyrazol-1-yl]benzenesulfonamide;
4-[3-(4-chlorophenyl)-5-(2,5-dimethoxyphenyl)-1H-pyrazol-1-yl]benzenesulfonamide;
4-[3-(4-chlorophenyl)-5-(2,6-dimethoxyphenyl)-1H-pyrazol-1-yl]benzenesulfonamide;
4-[3-(4-chlorophenyl)-5-(3,4-dimethoxyphenyl)-1H-pyrazol-1-yl]benzenesulfonamide;
4-[3-(4-chlorophenyl)-5-(2-trifluoromethylphenyl)-1H-pyrazol-1-yl]benzenesulfonamide;
4-[3-(4-chlorophenyl)-5-(3-trifluoromethylphenyl)-1H-pyrazol-1-yl]benzenesulfonamide;
4-[3-(4-chlorophenyl)-5-(4-trifluoromethylphenyl)-1H-pyrazol-1-yl]benzenesulfonamide;
4-[3-(4-chlorophenyl)-5-(2-aminophenyl)-1H-pyrazol-1-yl]benzenesulfonamide;
4-[3-(4-chlorophenyl)-5-(3-aminophenyl)-1H-pyrazol-1-yl]benzenesulfonamide;
4-[3-(4-chlorophenyl)-5-(4-aminophenyl)-1H-pyrazol-1-yl]benzenesulfonamide;
4-[3-(4-chlorophenyl)-5-(2-[N,N-dimethylamino]phenyl)-1H-pyrazol-1-yl]benzenesulfonamide;
4-[3-(4-chlorophenyl)-5-(3-[N,N-dimethylamino]phenyl)-1H-pyrazol-1-yl]benzenesulfonamide;
4-[3-(4-chlorophenyl)-5-(4-[N,N-dimethylamino]phenyl)-1H-pyrazol-1-yl]benzenesulfonamide;
4-[3-(4-chlorophenyl)-5-(4-methoxycarbonylphenyl)-1H-pyrazol-1yl]benzenesulfonamide;
4-[3-(4-chlorophenyl)-5-(2-methoxycarbonylphenyl)-1H-pyrazol-1yl]benzenesulfonamide;
4-[3-(4-chlorophenyl)-5-(2-nitrophenyl)-1H-pyrazol-1-yl]benzenesulfonamide;
4-[3-(4-chlorophenyl)-5-(3-nitrophenyl)-1H-pyrazol-1-yl]benzenesulfonamide;
4-[3-(4-chlorophenyl)-5-(4-nitrophenyl)-1H-pyrazol-1-yl]benzenesulfonamide;
4-[3-(4-chlorophenyl)-5-(2-methylthiophenyl)-1H-pyrazol-1-yl]benzenesulfonamide;
4-[3-(4-chlorophenyl)-5-(3-methylthiophenyl)-1H-pyrazol-1-yl]benzenesulfonamide;
4-[3-(4-chlorophenyl)-5-(4-methylthiophenyl)-1H-pyrazol-1-yl]benzenesulfonamide;
4-[3-(4-chlorophenyl)-5-(2-cyanophenyl)-1H-pyrazol-1-yl]benzenesulfonamide;
4-[3-(4-chlorophenyl)-5-(3-cyanophenyl)-1H-pyrazol-1-yl]benzenesulfonamide;
4-[3-(4-chlorophenyl)-5-(4-cyanophenyl)-1H-pyrazol-1-yl]benzenesulfonamide;
4-[3-(4-chlorophenyl)-5-(2-thienyl)-1H-pyrazol-1-yl]benzenesulfonamide;
4-[3-(4-chlorophenyl)-5-(3-thienyl)-1H-pyrazol-1-yl]benzenesulfonamide;
4-[3-(4-chlorophenyl)-5-(2-pyridyl)-1H-pyrazol-1-yl]benzenesulfonamide;
4-[3-(4-chlorophenyl)-5-(3-pyridyl)-1H-pyrazol-1-yl]benzenesulfonamide;
4-[3-(4-chlorophenyl)-5-(4-pyridyl)-1H-pyrazol-1-yl]benzenesulfonamide;
4-[3-(4-chlorophenyl)-5-(2-furanyl)-1H-pyrazol-1-yl]benzenesulfonamide;
4-[3-(4-chlorophenyl)-5-(3-furanyl)-1H-pyrazol-1-yl]benzenesulfonamide;
4-[3-(4-chlorophenyl)-5-(2-hydroxyphenyl)-1H-pyrazol-1-yl]benzenesulfonamide;
4-[3-(4-chlorophenyl)-5-(3-hydroxyphenyl)-1H-pyrazol-1-yl]benzenesulfonamide;
4-[3-(4-chlorophenyl)-5-(4-hydroxyphenyl)-1H-pyrazol-1-yl]benzenesulfonamide;
4-[3-(4-chlorophenyl)-5-(2-carboxyphenyl)-1H-pyrazol-1-yl]benzenesulfonamide;
4-[3-(4-chlorophenyl)-5-(3-carboxyphenyl)-1H-pyrazol-1-yl]benzenesulfonamide;
4-[3-(4-chlorophenyl)-5-(4-carboxyphenyl)-1H-pyrazol-1-yl]benzenesulfonamide;
4-[3-(4-chlorophenyl)-5-(2-methoxycarbonylphenyl)-1H-pyrazol-1-yl]benzenesulfonamide;
4-[3-(4-chlorophenyl)-5-(3-methoxycarbonylphenyl)-1H-pyrazol-1-yl]benzenesulfonamide;
4-[3-(4-chlorophenyl)-5-(3-ethoxycarbonylphenyl)-1H-pyrazol-1-yl]benzenesulfonamide;

4-[3-(4-chlorophenyl)-5-(4-ethoxycarbonylphenyl)-1H-pyrazol-1-yl]benzenesulfonamide;
4-[3-(4-chlorophenyl)-5-(2-acetamidophenyl)-1H-pyrazol-1-1-yl]benzenesulfonamide;
4-[3-(4-chlorophenyl)-5-(3-acetamidophenyl)-1H-pyrazol-1-1-yl]benzenesulfonamide;
4-[3-(4-chlorophenyl)-5-(4-acetamidophenyl)-1H-pyrazol-1-yl]benzensulfonamide;
4-[3-(4-chlorophenyl)-5-(2-bromophenyl)-1H-pyrazol-1-yl]benzenesulfonamide;
4-[3-(4-chlorophenyl)-5-(3-bromophenyl)-1H-pyrazol-1-yl]benzenesulfonamide;
4-[3-(4-chlorophenyl)-5-(4-bromophenyl)-1H-pyrazol-1-yl]benzenesulfonamide;
4-[3,5-bis(4-methoxyphenyl)-1H-pyrazol-1-yl]benzenesulfonamide;
4-[3,5-bis(4-methylphenyl)-1H-pyrazol-1-yl]benzenesulfonamide;
4-[3,5-bis(4-nitrophenyl)-1H-pyrazol-1-yl]benzenesulfonamide;
4-[3,5-bis(4-methylthiophenyl)-1H-pyrazol-1-yl]benzenesulfonamide;
4-[3,5-bis(4-aminophenyl)-1H-pyrazol-1-yl]benzenesulfonamide;
4-[3,5-bis(4-trifluoromethylphenyl)-1H-pyrazol-1-yl]benzenesulfonamide;
4-[3,5-bis(4-hydroxyphenyl)-1H-pyrazol-1-yl]benzenesulfonamide;
4-[3,5-bis(4-carboxyphenyl)-1H-pyrazol-1-yl]benzenesulfonamide;
4-[3,5-bis(4-cyanophenyl)-1H-pyrazol-1-yl]benzenesulfonamide;
4-[3,5-bis(4-bromophenyl)-1H-pyrazol-1-yl]benzenesulfonamide;
4-[3,5-bis(4-fluorophenyl)-1H-pyrazol-1-yl]benzenesulfonamide;
4-[3,5-bis(4-chlorophenyl)-4-methyl-1H-pyrazol-1-yl]benzenesulfonamide;
4-[3,5-bis(4-chlorophenyl)-4-ethyl-1H-pyrazol-1-yl]benzenesulfonamide;
4-[3,5-bis(4-chlorophenyl)-4-propyl-1H-pyrazol-1-yl]benzenesulfonamide;
4-[3,5-bis(4-chlorophenyl)-4-butyl-1H-pyrazol-1-yl]benzenesulfonamide;
4-[3,5-bis(4-chlorophenyl)-4-isopropyl-1H-pyrazol-1-yl]benzenesulfonamide;
4-[3,5-bis(4-chlorophenyl)-4-(trifluoromethyl)-1H-pyrazol-1-yl]benzenesulfonamide;
4-[3,5-bis(4-chlorophenyl)-4-cyano-1H-pyrazol-1-yl]benzenesulfonamide;
4-[3,5-bis(4-chlorophenyl)-4-(difluoromethyl)-1H-pyrazol-1-yl]benzenesulfonamide;
4-[3,5-bis(4-chlorophenyl)-4-carboxy-1H-pyrazol-1-yl]benzenesulfonamide;
4-[3,5-bis(4-chlorophenyl)-4-(methoxycarbonyl)-1H-pyrazol-1-yl]benzenesulfonamide;
4-[3,5-bis(4-chlorophenyl)-4-(ethoxycarbonyl)-1H-pyrazol-1-yl]benzenesulfonamide;
4-[3,5-bis(4-chlorophenyl)-4-acetyl-1H-pyrazol-1-yl]benzenesulfonamide;
4-[3,5-bis(4-chlorophenyl)-4-formyl-1H-pyrazol-1-yl]benzenesulfonamide;
4-[3,5-bis(4-chlorophenyl)-4-amino-1H-pyrazol-1-yl]benzenesulfonamide;
4-[3,5-bis(4-chlorophenyl)-4-acetamido-1H-pyrazol-1-yl]benzenesulfonamide;
4-[3,5-bis(4-chlorophenyl)-4-(N-[methylsulfonyl])amino-1H-pyrazol-1-yl]benzenesulfonamide;
4-[3,5-bis(4-chlorophenyl)-4-fluoro-1H-pyrazol-1-yl]benzenesulfonamide;
4-[3,5-bis(4-chlorophenyl)-4-chloro-1H-pyrazol-1-yl]benzenesulfonamide; and
4-[3,5-bis(4-chlorophenyl)-4-bromo-1H-pyrazol-1-yl]benzenesulfonamide.

Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "aryl", alone or in combination, means a carbocyclic aromatic system containing one, two or three rings wherein such rings may be attached together in a pendent manner or may be fused. Examples of "aryl" include phenyl, biphenyl or naphthyl radicals. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include pyrrolidyl and morpholinyl. The term "heteroaryl" is embraced by the term "heterocyclic" and includes unsaturated heterocyclic radicals. Examples of "heteroaryl" radicals include thienyl, pyrryl, furyl, pyridyl, pyrimidyl, pyrazinyl, pyrazolyl, oxazolyl, isoxazolyl, imidazolyl, thiazolyl, pyranyl and tetrazolyl. The term "alkoxy" embraces linear or branched oxy-containing radicals each having alkyl portions of one to about ten carbon atoms. The "alkoxy" or "alkoxyalkyl" radicals may be further substituted with one or more halo atoms, such as fluoro, chloro or bromo, to provide "haloalkoxy" or "haloalkoxyalkyl" radicals. Examples of "alkoxy" radicals include methoxy, butoxy and trifluoromethoxy. The term "halo" means halogens such as fluorine, chlorine, bromine or iodine atoms. The term "hydrido" denotes a single hydrogen atom (H). This hydrido radical may be attached, for example, to an oxygen atom to form a hydroxyl group or two hydrido radicals may be attached to a carbon atom to form a methylene ($-CH_2$) radical. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two of the same halo atoms or a combination of different halo radicals and polyhaloalkyl radicals may have more than two of the same halo atoms or a combination of different halo radicals. The term "sulfonyl", whether used alone or linked to other terms such as "alkylsulfonyl", denotes respectively divalent radicals $-SO_2-$. "Alkylsulfonyl", embraces alkyl radicals attached to a sulfonyl radical, where alkyl is defined as above. The terms "sulfamyl" or "sulfonamidyl" denotes a sulfonyl radical substituted with an amine radical, forming a sulfonamide ($-SO_2NH_2$). The terms "carboxy" or "carboxyl" denotes $-CO_2H$. The term "carbonyl", whether used alone or with other terms, such as "alkylcarbonyl", denotes $-(C=O)-$. The term "alkoxycarbonyl" means a radical containing an alkoxy radical, as defined above, attached via an oxygen atom to a carbonyl (C=O) radical. Examples of such "alkoxycarbonyl" radicals include ethoxycarbonyl (CH$_3$CH$_2$CO—C(=O)—) and methoxycarbonyl —(O=)C—OCH$_3$. The term "alkylthio" embraces radicals containing a linear or branched alkyl radical, of one to ten carbon atoms, attached to a divalent sulfur atom. An example of an "alkylthio" radical is methylthio, (CH$_3$—S—). The terms "N-monoalkylamino" and "N,N-dialkylamino" denote amino radicals which have been substituted with one alkyl radical and with two alkyl radicals, respectively. The term "acyl", whether used alone, or within a term such as "acylamino", denotes a radical provided by a residue after removal of hydroxyl from an organic acid. The term "acylamino" embraces an amino radical substituted with an acyl radical. An examples of an "acylamino" radical is the acetylamino or acetamido radical (CH$_3$C(=O)—NH—). The term "alkylsulfonylamino" denotes an amino radical substituted with an alkylsulfonyl radical as defined above. An example of an "alkylsulfonylamino" radical is methylsulfonylamino (CH$_3$SO$_2$NH—).

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL METHOD OF SYNTHESIS

The compounds of the invention can be synthesized according to the following procedures of Schemes I–II, wherein the R$^1$–R$^4$ substituents are as defined for Formula I, above, except where further noted. Synthetic Scheme I shows the preparation of tetrasubstituted pyrazoles from starting material 1. In step 1 of synthetic Scheme I, the phenyl-methyl ketone (1) is treated with a base (preferably a lithium base such as lithium diisopropylamide or LiHMDS) and an alkylating reagent (R$^3$X, where X represents a leaving group such as tosyl) to give the substituted ketone (2). In step 2, the substituted ketone (2) is treated with base, such as sodium methoxide, and an ester to give the intermediate diketone (3) in a procedure similar to that developed by Reid and Calvin, *J. Amer. Chem. Soc.*, 72, 2948–2952 (1950). In step 3, the diketone (3) is reacted with a substituted phenylhydrazine in acetic acid or an alcoholic solvent to give a mixture of pyrazoles (4) and (5). Separation of the desired pyrazole (4) can be achieved by chromatography or recrystallization.

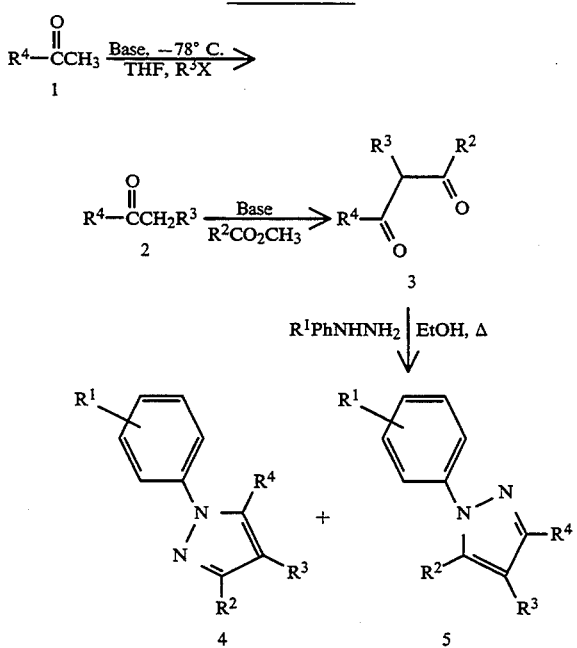

SCHEME I

Synthetic Scheme II shows the preparation of compounds embraced by Formula I, where R$^3$ is a hydrogen atom. In step 1, ketone (1) is treated with a base, preferably NaOMe or NaH, and an ester, or ester equivalent, to form the intermediate diketone (6) which is used without further purification. In step 2, diketone (6) in an anhydrous aprotic solvent, such as absolute ethanol or acetic acid, is treated with the free base or the hydrochloride salt of a phenylhydrazine at reflux for 24 hours to afford a mixture of pyrazoles (7) and (8). Recrystallization from diethyl ether/hexane or chromatography affords (7), usually as a light yellow or tan solid.

SCHEME II

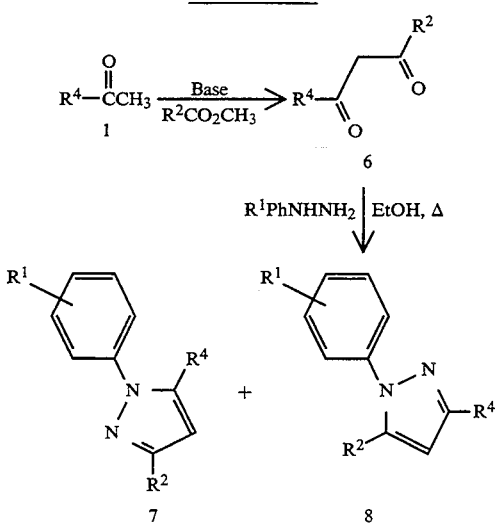

The following examples contain detailed descriptions of the methods of preparation of compounds of Formula I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

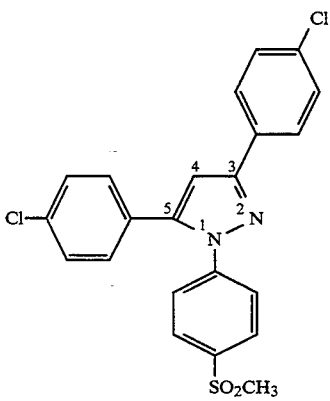

1-[4-(Methylsulfonyl)phenyl]-3,5-bis(4-chlorophenyl)-1H-pyrazole

Step 1: Preparation of 1,3-[4-chlorophenyl]-propane-1,3-dione.

Methyl-(4-chlorobenzoate) (8.20 g, 48 mmol) was placed in a 500 mL three-necked round bottom flask, and dissolved in tetrahydrofuran (30 mL). To the stirred solution was added 25 weight % sodium methoxide (11.50 g, 53 mmol) via an addition funnel over a 2 minute period. Next 4′-chloroacetophenone (6.83 g, 44 mmol) was added to the reaction dropwise over 5 minutes. After stirring overnight, 3N HCl (21 mL) was added. The organic layer was collected, washed with brine (75 mL), dried over MgSO$_4$, filtered, and concentrated in vacuo to give an orange solid. The solid was recrystallized from iso-octane/methylene chloride to give the dione (3.07 g, mp 158°–161° C.). M+H 292.

Step 2: Preparation of 1-[4-(methylsulfonyl)phenyl]-3,5-bis(4-chlorophenyl)-1H-pyrazole.

4-(Methylsulphonyl)phenylhydrazine hydrochloride (1.4 g, 6.2 mmol) is added to a stirred solution of 1,3-[4-chlorophenyl]-propane-1,3-dione (1.6 g, 5.4 mmol) in a mixture of ethanol (50 mL), acetone and acetonitrile. The reaction is heated to reflux and stirred. After cooling to room temperature, the reaction mixture is concentrated in vacuo. The residue is taken up in ethyl acetate and washed with water and brine and dried over MgSO$_4$, filtered, and concentrated in vacuo to give 1-[4-(methylsulfonyl)phenyl]-3,5-bis(4-chlorophenyl)-1H-pyrazole.

EXAMPLE 2

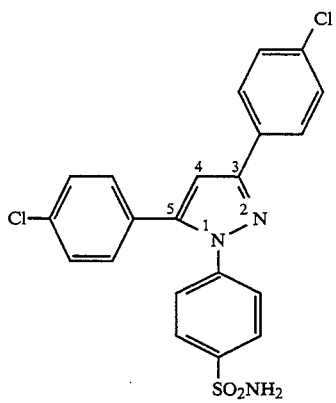

4-[3,5-Bis(4-chlorophenyl)-1H-pyrazol-1-yl]benzenesulfonamide

4-Sulphonamidophenyl hydrazine hydrochloride (982 mg, 4.4 mmol 1.1 equivalent) is added to a stirred solution of the previously described 1,3-[4-chlorophenyl]-propane-3-dione (1.17 g, 4.0 mmol) in ethanol (50 mL). The reaction is heated to reflux and stirred overnight. After cooling to room temperature, the reaction mixture is concentrated in vacuo. The residue is taken up in ethyl acetate and washed with water and brine and dried over MgSO$_4$, filtered, and concentrated in vacuo to give a light brown solid which is recrystallized from ethyl acetate and iso-octane to give 4-[3,5-bis(4-chlorophenyl)-1H-pyrazol-1-yl]benzenesulfonamide.

BIOLOGICAL EVALUATION

Rat Carrageenan Foot Pad Edema Test

The carrageenan foot edema test is performed essentially as described by Winter et al [*Proc. Soc. Exp. Biol. Med.*, 111, 544 (1962)]. Rats are dosed orally with compounds suspended in methylcellulose. One hour later a subplantar injection of 0.1 ml of 1% solution of carrageenan is administered and the volume of the injected foot is measured with a displacement plethysmometer. Three hours after the injection of the carrageenan the volume of the foot is again measured. The average foot swelling in a group of drug-treated animals is compared with that of a group of placebo-treated animals and the percentage inhibition of edema is determined (Otterness and Bliven, *Laboratory Models for Testing NSAIDS*, in *Non-Steroidal Anti-Inflammatory Drugs*, (J. Lombardino, ed. 1985)). The compounds of Formula I should be active in reducing inflammation in the Carrageenan paw assay at a dosage of 20 mg per kg body weight.

Rat Carrageenan-induced Analgesia Test

The analgesia assay using rat carrageenan is performed essentially as described by Hargreaves et al (Pain, 32, 77, 1988). Rats are treated exactly as described above for the carrageenan foot pad edema test. At the end of the three hour period the rats are placed in a plexiglass container and a light shone directly on either the injected fool or on the contralateral uninjected foot. The time until the rat withdraws its foot is then measured. The withdrawal latency in seconds is determined for the control and drug treated groups and percent inhibition of the hyperalgesic foot withdrawal determined. The compounds of Formula I should be active in the analgesia assay at a dosage of 20 mg per kg body weight.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

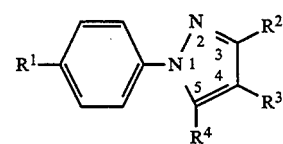

wherein $R^1$ is alkylsulfonyl or sulfamyl;

wherein $R^2$ is aryl; wherein $R^2$ is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino;

wherein $R^3$ is selected from hydrido, alkyl, haloalkyl, cyano, carboxyl, alkoxycarbonyl, amino, acyl, acylamino, halo and alkylsulfonylamino; and wherein $R^4$ is aryl; wherein $R^4$ is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino;

provided at least one of $R^2$ and $R^4$ cannot be phenyl when $R^1$ is sulfamyl; and further provided $R^2$ cannot be 4-methoxyphenyl or 4-methylphenyl when R⁴ is 4-methoxyphenyl or 4-methylphenyl, and when R¹ is sulfamyl;
or a pharmaceutically-acceptable salt thereof.

2. Compound of claim 1 wherein R¹ is lower alkylsulfonyl or sulfamyl; wherein R² is aryl; wherein R² is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein R³ is selected from hydrido, lower alkyl, lower haloalkyl, cyano, carboxyl, alkoxycarbonyl, amino, acyl, acylamino, halo and alkylsulfonylamino; and wherein R⁴ is aryl; wherein R⁴ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided at least one of R² and R⁴ cannot be phenyl when R¹ is sulfamyl; and further provided R² cannot be 4-methoxyphenyl or 4-methylphenyl when R⁴ is 4-methoxyphenyl or 4-methylphenyl and when R¹ is sulfamyl; or a pharmaceutically-acceptable salt thereof.

3. Compound of claim 2 wherein R¹ is lower alkylsulfonyl; wherein R² is aryl; wherein R² is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein R³ is selected from hydrido, lower alkyl, lower haloalkyl, cyano, carboxyl, alkoxycarbonyl, amino, acyl, acylamino, halo and alkylsulfonylamino; and wherein R⁴ is aryl; wherein R⁴ is optionally substituted at a substitutable position with one or more radicals selected from halo, lower alkoxy, lower alkyl, nitro, lower alkylthio, N,N-dialkylamino, cyano, alkoxycarbonyl and acylamino; or a pharmaceutically-acceptable salt thereof.

4. Compound of claim 3 wherein R¹ is methylsulfonyl; wherein R² is phenyl; wherein R² is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; wherein R³ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH-$; and wherein R⁴ is phenyl; wherein R⁴ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; or a pharmaceutically-acceptable salt thereof.

5. Compound of claim 2 wherein R¹ is sulfamyl; wherein R² is aryl; wherein R² is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein R³ is selected from hydrido, lower alkyl, lower haloalkyl, cyano, carboxyl, alkoxycarbonyl, amino, acyl, acylamino, halo and alkylsulfonylamino; and wherein R⁴ is aryl; wherein R⁴ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided at least one of R² and R⁴ cannot be phenyl; and further provided R² cannot be 4-methoxyphenyl or 4-methylphenyl when R⁴ is 4-methoxyphenyl or 4-methylphenyl; or a pharmaceutically-acceptable salt thereof.

6. Compound of claim 5 wherein R² is phenyl; wherein R² is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; wherein R³ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH$—; and wherein $R^4$ is phenyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; provided at least one of $R^2$ and $R^4$ cannot be phenyl; and further provided $R^2$ cannot be 4-methoxyphenyl or 4-methylphenyl when $R^4$ is 4-methoxyphenyl or 4-methylphenyl; or a pharmaceutically-acceptable salt thereof.

7. Compound of claim 4 selected from compounds, and their pharmaceutically-acceptable salts, of the group of compounds consisting of 1-(4-methylsulfonylphenyl)-3,5-bis(4-chlorophenyl)-pyrazole;
1-(4-methylsulfonylphenyl)-3-(3,4-difluorophenyl)-5-(4-chlorophenyl)pyrazole;
1-(4-methylsulfonylphenyl)-3-(4-methoxyphenyl)-5-(4-chlorophenyl)pyrazole;
1-(4-methylsulfonylphenyl)-3-(4-methylphenyl)-5-(4-chlorophenyl)pyrazole;
1-(4-methylsulfonylphenyl)-3-(4-nitrophenyl)-5-(4-chlorophenyl)pyrazole;
1-(4-methylsulfonylphenyl)-3-(4-methylthiophenyl)-5-(4-chlorophenyl)pyrazole;
1-(4-methylsulfonylphenyl)-3-(4-aminophenyl)-5-(4-chlorophenyl)pyrazole;
1-(4-methylsulfonylphenyl)-3-(4-trifluoromethylphenyl)-5-(4-chlorophenyl)pyrazole;
1-(4-methylsulfonylphenyl)-3-(4-hydroxyphenyl)-5-(4-chlorophenyl)pyrazole;
1-(4-methylsulfonylphenyl)-3-(4-carboxyphenyl)-5-(4-chlorophenyl)pyrazole;
1-(4-methylsulfonylphenyl)-3-(4-[N-methylamino]phenyl)-5-(4-chlorophenyl)pyrazole;
1-(4-methylsulfonylphenyl)-3-(4-acetamidophenyl)-5-(4-chlorophenyl)pyrazole;
1-(4-methylsulfonylphenyl)-3-(4-cyanophenyl)-5-(4-chlorophenyl)pyrazole;
1-(4-methylsulfonylphenyl)-3-(4-fluorophenyl)-5-(4-chlorophenyl)pyrazole;
1-(4-methylsulfonylphenyl)-3-phenyl -5-(4-chlorophenyl)pyrazole;
1-(4-methylsulfonylphenyl)-3-(4-chlorophenyl)-5-(phenyl)pyrazole;
1-(4-methylsulfonylphenyl)-3-(4-chlorophenyl)-5-(4-fluorophenyl)pyrazole;
1-(4-methylsulfonylphenyl)-3-(4-chlorophenyl)-5-(4-methylphenyl)pyrazole;
1-(4-methylsulfonylphenyl)-3-(4-chlorophenyl)-5-(4-methoxyphenyl)pyrazole;
1-(4-methylsulfonylphenyl)-3-(4-chlorophenyl)-5-(4-trifluoromethylphenyl)pyrazole;
1-(4-methylsulfonylphenyl)-3-(4-chlorophenyl)-5-(4-aminophenyl)pyrazole;
1-(4-methylsulfonylphenyl)-3-(4-chlorophenyl)-5-(4-methoxycarbonylphenyl)pyrazole;
1-(4-methylsulfonylphenyl)-3-(4-chlorophenyl)-5-(4-nitrophenyl)pyrazole;
1-(4-methylsulfonylphenyl)-3-(4-chlorophenyl)-5-(4-methylthiophenyl)pyrazole;
1-(4-methylsulfonylphenyl)-3-(4-chlorophenyl)-5-(4-cyanophenyl)pyrazole;
1-(4-methylsulfonylphenyl)-3-(4-chlorophenyl)-5-(4-hydroxyphenyl)pyrazole;
1-(4-methylsulfonylphenyl)-3-(4-chlorophenyl)-5-(4-carboxyphenyl)pyrazole;
1-(4-methylsulfonylphenyl)-3-(4-chlorophenyl)-5-(4-ethoxycarbonylphenyl)pyrazole;
1-(4-methylsulfonylphenyl)-3-(4-chlorophenyl)-5-(4-acetamidophenyl)pyrazole;
1-(4-methylsulfonylphenyl)-3,5-bis(4-chlorophenyl)-4-methyl-pyrazole;
1-(4-methylsulfonylphenyl)-3,5-bis(4-chlorophenyl)-4-trifluoromethyl-pyrazole;
1-(4-methylsulfonylphenyl)-3,5-bis(4-chlorophenyl)-4-cyano-pyrazole;
1-(4-methylsulfonylphenyl)-3,5-bis(4-chlorophenyl)-4-difluoromethyl-pyrazole;
1-(4-methylsulfonylphenyl)-3,5-bis(4-chlorophenyl)-4-carboxy-pyrazole;
1-(4-methylsulfonylphenyl)-3,5-bis(4-chlorophenyl)-4-methoxycarbonyl-pyrazole;
1-(4-methylsulfonylphenyl)-3,5-bis(4-chlorophenyl)-4-amino-pyrazole;
1-(4-methylsulfonylphenyl)-3,5-bis(4-chlorophenyl)-4-acetamido-pyrazole;
1-(4-methylsulfonylphenyl)-3,5-bis(4-chlorophenyl)-4-fluoro-pyrazole; and
1-(4-methylsulfonylphenyl)-3,5-bis(4-chlorophenyl)-4-chloro-pyrazole.

8. Compound of claim 6 selected from compounds, and their pharmaceutically-acceptable salts, of the group of compounds consisting of 4-[3,5-bis(4-chlorophenyl)-1H-pyrazol-1-yl]benzenesulfonamide;
4-[3-(3,4-difluorophenyl)-5-(4-chlorophenyl)-1H-pyrazol-1-yl]benzenesulfonamide;
4-[3-(4-methoxyphenyl)-5-(4-chlorophenyl)-1H-pyrazol-1-yl]benzenesulfonamide;
4-[3-(4-methylphenyl)-5-(4-chlorophenyl)-1H-pyrazol-1-yl]benzenesulfonamide;
4-[3-(4-nitrophenyl)-5-(4-chlorophenyl)-1H-pyrazol-1-yl]benzenesulfonamide;
4-[3-(4-methylthiophenyl)-5-(4-chlorophenyl)-1H-pyrazol-1-yl]benzenesulfonamide;
4-[3-(4-aminophenyl)-5-(4-chlorophenyl)-1H-pyrazol-1-yl]benzenesulfonamide;
4-[3-(4-trifluoromethylphenyl)-5-(4-chlorophenyl)-1H-pyrazol -1-yl]benzenesulfonamide;
4-[3-(4-hydroxyphenyl)-5-(4-chlorophenyl)-1H-pyrazol-1-yl]benzenesulfonamide;
4-[3-(4-carboxyphenyl)-5-(4-chlorophenyl)-1H-pyrazol-1-yl]benzenesulfonamide;
4-[3-(4-[N-methylamino]phenyl)-5-(4-chlorophenyl)-1H-pyrazol-1-yl]benzenesulfonamide;
4-[3-(4-acetamidophenyl)-5-(4-chlorophenyl)-1H-pyrazol -1-yl]benzenesulfonamide;
4-[3-(4-cyanophenyl)-5-(4-chlorophenyl)-1H-pyrazol-1-yl]benzenesulfonamide;
4-[3-(4-fluorophenyl)-5-(4-chlorophenyl)-1H-pyrazol-1-yl]benzenesulfonamide;

4-[3-(4-chlorophenyl)-5-(4-fluorophenyl)-1H-pyrazol-1-yl]benzenesulfonamide;
4-[3-(4-chlorophenyl)-5-(4-methylphenyl)-1H-pyrazol-1-yl]benzenesulfonamide;
4-[3-(4-chlorophenyl)-5-(4-methoxyphenyl)-1H-pyrazol-1-yl]benzenesulfonamide;
4-[3-(4-chlorophenyl)-5-(4-trifluoromethylphenyl)-1H-pyrazol-1-yl]benzenesulfonamide;
4-[3-(4-chlorophenyl)-5-(4-aminophenyl)-1H-pyrazol-1-yl]benzenesulfonamide;
4-[3-(4-chlorophenyl)-5-(4-methoxycarbonylphenyl)-1H-pyrazol-1-yl]benzenesulfonamide;
4-[3-(4-chlorophenyl)-5-(4-nitrophenyl)-1H-pyrazol-1-yl]benzenesulfonamide;
4-[3-(4-chlorophenyl)-5-(4-methylthiophenyl)-1H-pyrazol-1-yl]benzenesulfonamide;
4-[3-(4-chlorophenyl)-5-(4-cyanophenyl)-1H-pyrazol-1-yl]benzenesulfonamide;
4-[3-(4-chlorophenyl)-5-(4-hydroxyphenyl)-1H-pyrazol-1-yl]benzenesulfonamide;
4-[3-(4-chlorophenyl)-5-(4-carboxyphenyl)-1H-pyrazol-1-yl]benzenesulfonamide;
4-[3-(4-chlorophenyl)-5-(4-ethoxycarbonylphenyl)-1H-pyrazol-1-yl]benzenesulfonamide;
4-[3-(4-chlorophenyl)-5-(4-acetamidophenyl)-1H-pyrazol-1-yl]benzenesulfonamide;
4-[3,5-bis(4-chlorophenyl)-4-methyl-1H-pyrazol-1-yl]benzenesulfonamide;
4-[3,5-bis(4-chlorophenyl)-4-(trifluoromethyl)-1H-pyrazol-1-yl]benzenesulfonamide;
4-[3,5-bis(4-chlorophenyl)-4-cyano-1H-pyrazol-1-yl]benzenesulfonamide;
4-[3,5-bis(4-chlorophenyl)-4-(difluoromethyl)-1H-pyrazol -1-yl]benzenesulfonamide;
4-[3,5-bis(4-chlorophenyl)-4-carboxy-1H-pyrazol-1-yl]benzenesulfonamide;
4-[3,5-bis(4-chlorophenyl)-4-(methoxycarbonyl)-1H-pyrazol -1-yl]benzenesulfonamide;
4-[3,5-bis(4-chlorophenyl)-4-amino-1H-pyrazol-1-yl]benzenesulfonamide;
4-[3,5-bis(4-chlorophenyl)-4-acetamido-1H-pyrazol -1-yl]benzenesulfonamide;
4-[3,5-bis(4-chlorophenyl)-4-fluoro-1H-pyrazol-1-yl]benzenesulfonamide; and
4-[3,5-bis(4-chlorophenyl)-4-chloro-1H-pyrazol-1-yl]benzenesulfonamide.

9. A pharmaceutical composition comprising a therapeutically-effective amount of a compound and a pharmaceutically-acceptable carrier or diluent, said compound selected from a family of compounds of Formula I

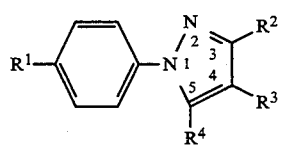

wherein $R^1$ is alkylsulfonyl or sulfamyl; wherein $R^2$ is aryl; wherein $R^2$ is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino;

wherein $R^3$ is selected from hydrido, alkyl, haloalkyl, cyano, carboxyl, alkoxycarbonyl, amino, acyl, acylamino, halo and alkylsulfonylamino; and wherein $R^4$ is aryl; wherein $R^4$ is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino;

provided at least one of $R^2$ and $R^4$ cannot be phenyl when $R^1$ is sulfamyl; and further provided $R^2$ cannot be 4-methoxyphenyl or 4-methylphenyl when $R^4$ is 4-methoxyphenyl or 4-methylphenyl, and when $R^1$ is sulfamyl;

or a pharmaceutically-acceptable salt thereof.

10. The composition of claim 9 wherein $R^1$ is lower alkylsulfonyl or sulfamyl; wherein $R^2$ is aryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; and wherein $R^4$ is aryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided at least one of $R^2$ and $R^4$ cannot be phenyl when $R^1$ is sulfamyl; and further provided $R^2$ cannot be 4-methoxyphenyl or 4-methylphenyl when $R^4$ is 4-methoxyphenyl or 4-methylphenyl and when $R^1$ is sulfamyl; or a pharmaceutically-acceptable salt thereof.

11. The composition of claim 10 wherein $R^1$ is lower alkylsulfonyl; wherein $R^2$ is aryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; and wherein $R^4$ is aryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; or a pharmaceutically-acceptable salt thereof.

12. The composition of claim 11 where $R^1$ is methylsulfonyl; wherein $R^2$ is phenyl; wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N- methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH—$; and wherein $R^4$ is phenyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; or a pharmaceutically-acceptable salt thereof.

13. The composition of claim 10 wherein $R^1$ is sulfamyl; wherein $R^2$ is aryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; and wherein $R^4$ is aryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided at least one of $R^2$ and $R^4$ cannot be phenyl; and further provided $R^2$ cannot be 4-methoxyphenyl or 4-methylphenyl when $R^4$ is 4-methoxyphenyl or 4-methylphenyl; or a pharmaceutically-acceptable salt thereof.

14. The composition of claim 13 wherein $R^2$ is phenyl; wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amino, acetyl, formyl acetamido, fluoro, chloro, iodo, bromo and $CH_3SO_2NH—$; and wherein $R^4$ is phenyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; provided at least one of $R^2$ and $R^4$ cannot be phenyl; and further provided $R^2$ cannot be 4-methoxyphenyl or 4-methylphenyl when $R^4$ is 4-methoxyphenyl or 4-methylphenyl; or a pharmaceutically-acceptable salt thereof.

15. The composition of claim 12 wherein said compound is selected from compounds, and their pharmaceutically-acceptable salts, of the group consisting of 1-(4-methylsulfonylphenyl)-3,5-bis(4-chlorophenyl)-pyrazole;

1-(4-methylsulfonylphenyl)-3-(3,4-difluorophenyl)-5-(4-chlorophenyl)pyrazole;

1-(4-methylsulfonylphenyl)-3-(4-methoxyphenyl)-5-(4-chlorophenyl)pyrazole;

1-(4-methylsulfonylphenyl)-3-(4-methylphenyl)-5-(4-chlorophenyl)pyrazol;

1-(4-methylsulfonylphenyl)-3-(4-nitrophenyl)-5-(4-chlorophenyl)pyrazole;

1-(4-methylsulfonylphenyl)-3-(4-methylthiophenyl)-5-(4-chlorophenyl)pyrazole;

1-(4-methylsulfonylphenyl)-3-(4-aminophenyl)-5-(4-chlorophenyl)pyrazole;

1-(4-methylsulfonylphenyl)-3-(4-trifluoromethylphenyl)-5-(4-chlorophenyl)pyrazole;

1-(4-methylsulfonylphenyl)-3-(4-hydroxyphenyl)-5-(4-chlorophenyl)pyrazole;

1-(4-methylsulfonylphenyl)-3-(4-carboxyphenyl)-5-(4-chlorophenyl)pyrazole;

1-(4-methylsulfonylphenyl)-3-(4-[N-methylamino]phenyl)-5-(4-chlorophenyl)pyrazole;

1-(4-methylsulfonylphenyl)-3-(4-acetamidophenyl)-5-(4-chlorophenyl)pyrazole;

1-(4-methylsulfonylphenyl)-3-(4-cyanophenyl-5-(4-chlorophenyl)pyrazole;

1-(4-methylsulfonylphenyl)-3-(4-fluorophenyl)-5-(4-chlorophenyl)pyrazole;

1-(4-methylsulfonylphenyl)-3-phenyl-5-(4-chlorophenyl)pyrazole;
1-(4-methylsulfonylphenyl)-3-(4-chlorophenyl)-5-(phenyl)pyrazole;
1-(4-methylsulfonylphenyl)-3-(4-chlorophenyl)-5-(4-fluorophenyl)pyrazole;
1-(4-methylsulfonylphenyl)-3-(4-chlorophenyl)-5-(4-methylphenyl)pyrazole;
1-(4-methylsulfonylphenyl)-3-(4-chlorophenyl)-5-(4-methoxyphenyl)pyrazole;
1-(4-methylsulfonylphenyl)-3-(4-chlorophenyl)-5-(4-trifluoromethylphenyl)pyrazol;
1-(4-methylsulfonylphenyl)-3-(4-chlorophenyl)-5-(4-aminophenyl)pyrazole;
1-(4-methylsulfonylphenyl)-3-(4-chlorophenyl)-5-(4-methoxycarbonylphenyl)pyrazole;
1-(4-methylsulfonylphenyl)-3-(4-chlorophenyl)-5-(4-nitrophenyl)pyrazole;
1-(4-methylsulfonylphenyl)-3-(4-chlorophenyl)-5-(4-methylthiophenyl)pyrazole;
1-(4-methylsulfonylphenyl)-3-(4-chlorophenyl)-5-(4-cyanophenyl)pyrazole;
1-(4-methylsulfonylphenyl)-3-(4-chlorophenyl)-5-(4-hydroxyphenyl)pyrazole;
1-(4-methylsulfonylphenyl)-3-(4-chlorophenyl)-5-(4-carboxyphenyl)pyrazole;
1-(4-methylsulfonylphenyl)-3-(4-chlorophenyl)-5-(4-ethoxycarbonylphenyl)pyrazole;
1-(4-methylsulfonylphenyl)-3-(4-chlorophenyl)-5-(4-acetamidophenyl)pyrazole;
1-(4-methylsulfonylphenyl)-3,5-bis(4-chlorophenyl)-4-methyl-pyrazole;
1-(4-methylsulfonylphenyl)-3,5-bis(4-chlorophenyl)-4-trifluoromethyl-pyrazole;
1-(4-methylsulfonylphenyl)-3,5-bis(4-chlorophenyl)-4-cyano-pyrazole;
1-(4-methylsulfonylphenyl)-3,5-bis(4-chlorophenyl)-4-difluoromethyl-pyrazole;
1-(4-methylsulfonylphenyl)-3,5-bis(4-chlorophenyl)-4-carboxy-pyrazole;
1-(4-methylsulfonylphenyl)-3,5-bis(4-chlorophenyl)-4-methoxycarbonyl-pyrazole;
1-(4-methylsulfonylphenyl)-3,5-bis(4-chlorophenyl)-4-amino-pyrazole;
1-(4-methylsulfonylphenyl)-3,5-bis(4-chlorophenyl)-4-acetamido-pyrazole;
1-(4-methylsulfonylphenyl)-3,5-bis(4-chlorophenyl)-4-fluoro-pyrazole; and
1-(4-methylsulfonylphenyl)-3,5-bis(4-chlorophenyl)-4-chloro-pyrazole.

16. The composition of claim 14 wherein said compound is selected from compounds, and their pharmaceutically-acceptable salts, of the group consisting of
4-[3,5-bis(4-chlorophenyl)-1H-pyrazol-1-yl]benzenesulfonamide;
4-[3-(3,4-difluorophenyl)-5-(4-chlorophenyl)-1H-pyrazol-1-yl]benzenesulfonamide;
4-[3-(4-methoxyphenyl)-5-(4-chlorophenyl)-1H-pyrazol-1-yl]benzenesulfonamide;
4-[3-(4-methylphenyl)-5-(4-chlorophenyl)-1H-pyrazol-1-yl]benzenesulfonamide;
4-[3-(4-nitrophenyl)-5-(4-chlorophenyl)-1H-pyrazol-1-yl]benzenesulfonamide;
4-[3-(4-methylthiophenyl)-5-(4-chlorophenyl)-1H-pyrazol-1-yl]benzenesulfonamide;
4-[-3-(4-aminophenyl)-5-(4-chlorophenyl)-1H-pyrazol-1-yl]benzenesulfonamide;
4-[3-(4-trifluoromethylphenyl)-5-(4-chlorophenyl)-1H-pyrazol-1-yl]benzenesulfonamide;
4-[3-(4-hydroxyphenyl)-5-(4-chlorophenyl)-1H-pyrazol-1-yl]benzenesulfonamide;
4-[3-(4-carboxyphenyl)-5-(4-chlorophenyl)-1H-pyrazol-1-yl]benzenesulfonamide;
4-[3-(4-[N-methylamino]phenyl)-5-(4-chlorophenyl)-1H-pyrazol-1-yl]benzenesulfonamide;
4-[3-(4-acetamidophenyl)-5-(4-chlorophenyl)-1H-pyrazol-1-yl]benzenesulfonamide;
4-[3-(4-cyanophenyl)-5-(4-chlorophenyl)-1H-pyrazol-1-yl]benzenesulfonamide;
4-[3-(4-fluorophenyl)-5-(4-chlorophenyl)-1H-pyrazol-1-yl]benzenesulfonamide;
4-[3-(4-chlorophenyl)-5-(4-fluorophenyl)-1H-pyrazol-1-yl]benzenesulfonamide;
4-[3-(4-chlorophenyl)-5-(4-methylphenyl)-1H-pyrazol-1-yl]benzenesulfonamide;
4-[3-(4-chlorophenyl)-5-(4-methoxyphenyl)-1H-pyrazol-1-yl]benzenesulfonamide;
4-[3-(4-chlorophenyl)-5-(4-trifluoromethylphenyl)-1H-pyrazol-1-yl]benzenesulfonamide;
4-[3-(4-chlorophenyl)-5-(4-aminophenyl)-1H-pyrazol-1-yl]benzenesulfonamide;
4-[3-(4-chlorophenyl)-5-(4-methoxycarbonylphenyl)-1H-pyrazol-1-yl]benzenesulfonamide;
4-[3-(4-chlorophenyl)-5-(4-nitrophenyl)-1H-pyrazol-1-yl]benzenesulfonamide;
4-[3-(4-chlorophenyl)-5-(4-methylthiophenyl)-1H-pyrazol-1-yl]benzenesulfonamide;
4-[3-(4-chlorophenyl)-5-(4-cyanophenyl)-1H-pyrazol-1-yl]benzenesulfonamide;
4-[3-(4-chlorophenyl)-5-(4-hydroxyphenyl)-1H-pyrazol-1-yl]benzenesulfonamide;
4-[3-(4-chlorophenyl)-5-(4-carboxyphenyl)-1H-pyrazol-1-yl]benzenesulfonamide;
4-[3-(4-chlorophenyl)-5-(4-ethoxycarbonylphenyl)-1H-pyrazol-1-yl]benzenesulfonamide;
4-[3-(4-chlorophenyl)-5-(4-acetamidophenyl)-1H-pyrazol-1-yl]benzenesulfonamide;
4-[3,5-bis(4-chlorophenyl)-4-methyl-1H-pyrazol-1-yl]benzenesulfonamide;
4-[3,5-bis(4-chlorophenyl)-4-(trifluoromethyl)-1H-pyrazol-1-yl]benzenesulfonamide;
4-[3,5-bis(4-chlorophenyl)-4-cyano-1H-pyrazol-1-yl]benzenesulfonamide;
4-[3,5-bis(4-chlorophenyl)-4-(difluoromethyl)-1H-pyrazol-1-yl]benzenesulfonamide;
4-[3,5-bis(4-chlorophenyl)-4-carboxy-1H-pyrazol-1-yl]benzenesulfonamide;
4-[3,5-bis(4-chlorophenyl)-4-methoxycarbonyl-1H-pyrazol-1-yl]benzenesulfonamide;
4-[3,5-bis(4-chlorophenyl)-4-amino-1H-pyrazol-1-yl]benzenesulfonamide;
4-[3,5-bis(4-chlorophenyl)-4-acetamido-1H-pyrazol-1-yl]benzenesulfonamide;
4-[3,5-bis(4-chlorophenyl)-4-fluoro-1H-pyrazol-1-yl]benzenesulfonamide; and
4-[3,5-bis(4-chlorophenyl)-4-chloro-1H-pyrazol-1-yl]benzenesulfonamide.

17. A therapeutic method of treating inflammation or an inflammation-related disorder, said method comprising administering to a subject having such inflammation or inflammation-related disorder, a therapeutically-effective amount of a compound of Formula I

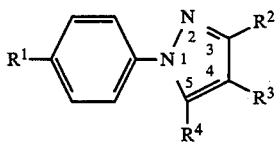

wherein R¹ is alkylsulfonyl or sulfamyl;

wherein R² is aryl; wherein R² is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino;

wherein R³ is selected from hydrido, alkyl, haloalkyl, cyano, carboxyl, alkoxycarbonyl, amino, acyl, acylamino, halo and alkylsulfonylamino; and wherein R⁴ is aryl; wherein R⁴ is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino;

or a pharmaceutically-acceptable salt thereof.

18. The method of claim 17 wherein R¹ is lower alkylsulfonyl or sulfamyl; wherein R² is aryl; wherein R² is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein R³ is selected from hydrido, lower alkyl, lower haloalkyl, cyano, carboxyl, alkoxycarbonyl, amino, acyl, acylamino, halo and alkylsulfonylamino; and wherein R⁴ is aryl; wherein R⁴ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; or a pharmaceutically-acceptable salt thereof.

19. The method of claim 18 wherein R¹ is lower alkylsulfonyl; wherein R² is aryl; wherein R² is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein R³ is selected from hydrido, lower alkyl, lower haloalkyl, cyano, carboxyl, alkoxycarbonyl, amino, acyl, acylamino, halo and alkylsulfonylamino; and wherein R⁴ is aryl; wherein R⁴ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; or a pharmaceutically-acceptable salt thereof.

20. The method of claim 19 wherein R¹ is methylsulfonyl; wherein R² is phenyl; wherein R² is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; wherein R³ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH$—; and wherein R⁴ is phenyl; wherein R⁴ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; or a pharmaceutically-acceptable salt thereof.

21. The method of claim 18 wherein R¹ is sulfamyl; wherein R² is aryl; wherein R² is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein R³ is selected from hydrido, lower alkyl, lower haloalkyl, cyano, carboxyl, alkoxycarbonyl, amino, acyl, acylamino, halo and alkylsulfonylamino; and wherein R⁴ is aryl; wherein R⁴ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; or a pharmaceutically-acceptable salt thereof.

22. The method of claim 21 wherein R² is phenyl; wherein R² is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N- isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH$—; and wherein $R^4$ is phenyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and acetamido; or a pharmaceutically-acceptable salt thereof.

23. The method of claim 20 selected from compounds, and their pharmaceutically-acceptable salts, of the group of compounds consisting of
1-(4-methylsulfonylphenyl)-3,5-bis(4-chlorophenyl)-pyrazole;
1-(4-methylsulfonylphenyl)-3-(3,4-difluorophenyl)-5-(4-chlorophenyl)pyrazol;
1-(4-methylsulfonylphenyl)-3-(4-methoxyphenyl)-5-(4-chlorophenyl)pyrazol;
1-(4-methylsulfonylphenyl)-3-(4-methylphenyl)-5-(4-chlorophenyl)pyrazol;
1-(4-methylsulfonylphenyl)-3-(4-nitrophenyl)-5-(4-chlorophenyl)pyrazol;
1-(4-methylsulfonylphenyl)-3-(4-methylthiophenyl)-5-(4-chlorophenyl)pyrazol;
1-(4-methylsulfonylphenyl)-3-(4-aminophenyl)-5-(4-chlorophenyl)pyrazol;
1-(4-methylsulfonylphenyl)-3-(4-trifluoromethylphenyl)-5-(4-chlorophenyl)pyrazol;
1-(4-methylsulfonylphenyl)-3-(4-hydroxyphenyl)-5-(4-chlorophenyl)pyrazol;
1-(4-methylsulfonylphenyl)-3-(4-carboxyphenyl)-5-(4-chlorophenyl)pyrazol;
1-(4-methylsulfonylphenyl)-3-(4-[N-methylamino]-phenyl)-5-(4-chlorophenyl)pyrazol;
1-(4-methylsulfonylphenyl)-3-(4-acetamidophenyl)-5-(4-chlorophenyl)pyrazol;
1-(4-methylsulfonylphenyl)-3-(4-cyanophenyl)-5-(4-chlorophenyl)pyrazole;
1-(4-methylsulfonylphenyl)-3-(4-fluorophenyl)-5-(4-chlorophenyl)pyrazole;
1-(4-methylsulfonylphenyl)-3-phenyl-5-(4-chlorophenyl)pyrazole;
1-(4-methylsulfonylphenyl)-3-(4-chlorophenyl)-5-(phenyl)pyrazole;
1-(4-methylsulfonylphenyl)-3-(4-chlorophenyl)-5-(4-fluorophenyl)pyrazol;
1-(4-methylsulfonylphenyl)-3-(4-chlorophenyl)-5-(4-methylphenyl)pyrazol;
1-(4-methylsulfonylphenyl)-3-(4-chlorophenyl)-5-(4-methoxyphenyl)pyrazole;
1-(4-methylsulfonylphenyl)-3-(4-chlorophenyl)-5-(4-trifluoromethylphenyl)pyrazole;
1-(4-methylsulfonylphenyl)-3-(4-chlorophenyl)-5-(4-aminophenyl)pyrazole;
1-(4-methylsulfonylphenyl)-3-(4-chlorophenyl)-5-(4-methoxycarbonylphenyl)pyrazole;
1-(4-methylsulfonylphenyl)-3-(4-chlorophenyl)-5-(4-nitrophenyl)pyrazole;
1-(4-methylsulfonylphenyl)-3-(4-chlorophenyl -5-(4-methylthiophenyl)pyrazole;
1-(4-methylsulfonylphenyl)-3-(4-chlorophenyl -5-(4-cyanophenyl)pyrazole;
1-(4-methylsulfonylphenyl)-3-(4-chlorophenyl -5-(4-hydroxyphenyl)pyrazole;
1-(4-methylsulfonylphenyl)-3-(4-chlorophenyl -5-(4-carboxyphenyl)pyrazole;
1-(4-methylsulfonylphenyl)-3-(4-chlorophenyl -5-(4-ethoxycarbonylphenyl)pyrazole;
1-(4-methylsulfonylphenyl)-3-(4-chlorophenyl)-5-(4-acetamidophenyl)pyrazole;
1-(4-methylsulfonylphenyl)-3,5-bis(4-chlorophenyl)-4-methyl-pyrazole;
1-(4-methylsulfonylphenyl)-3,5-bis(4-chlorophenyl)-4-trifluoromethyl-pyrazole;
1-(4-methylsulfonylphenyl)-3,5-bis(4-chlorophenyl)-4-cyano-pyrazole;
1-(4-methylsulfonylphenyl)-3,5-bis(4-chlorophenyl)-4-difluoromethyl-pyrazole;
1-(4-methylsulfonylphenyl)-3,5-bis(4-chlorophenyl)-4-carboxy-pyrazole;
1-(4-methylsulfonylphenyl)-3,5-bis(4-chlorophenyl)-4-methoxycarbonyl-pyrazole;
1-(4-methylsulfonylphenyl)-3,5-bis(4-chlorophenyl)-4-amino-pyrazole;
1-(4-methylsulfonylphenyl)-3,5-bis(4-chlorophenyl)-4-acetamido-pyrazole;
1-(4-methylsulfonylphenyl)-3,5-bis(4-chlorophenyl)-4-fluoro-pyrazole; and
1-(4-methylsulfonylphenyl)-3,5-bis(4-chlorophenyl)-4-chloro-pyrazole.

24. The method of claim 22 wherein said compound is selected from compounds, and their pharmaceutically-acceptable salts, of the group consisting of
4-[3,5-bis 4-chlorophenyl)-1H-pyrazol-1-yl]benzenesulfonamide;
4-[3-(3,4-difluorophenyl)-5-(4-chlorophenyl)-1H-pyrazol-yl]benzenesulfonamide;
4-[3-(4-methoxyphenyl)-5-(4-chlorophenyl)-1H-pyrazol-1-yl]benzenesulfonamide;
4-[3-(4-methylphenyl)-5-(4-chlorophenyl)-1H-pyrazol-1-yl]benzenesulfonamide;
4-[3-(4-nitrophenyl)-5-(4-chlorophenyl)-1H-pyrazol-1-yl]benzenesulfonamide;
4-[3-(4-methylthiophenyl)-5-(4-chlorophenyl)-1H-pyrazol-1-yl]benzenesulfonamide;
4-[-3-(4-aminophenyl)-5-(4-chlorophenyl)-1H-pyrazol-1-yl]benzenesulfonamide;

4-[3-(4-trifluoromethylphenyl)-5-(4-chlorophenyl)-1H-pyrazol-1-yl]benzenesulfonamide;
4-[3-(4-hydroxyphenyl)-5-(4-chlorophenyl)-1H-pyrazol-1-yl]benzenesulfonamide;
4-[3-(4-carboxyphenyl)-5-(4-chlorophenyl)-1H-pyrazol-1-yl]benzenesulfonamide;
4-[3-(4-[N-methylamino]phenyl)-5-(4-chlorophenyl)-1H-pyrazol-1-yl]benzensulfonamide;
4-[3-(4-acetamidophenyl)-5-(4-chlorophenyl)-1H-pyrazol-1-yl]benzenesulfonamide;
4-[3-(4-cyanophenyl)-5-(4-chlorophenyl)-1H-pyrazol-1-yl]benzensulfonamide;
4-[3-(4-fluorophenyl)-5-(4-chlorophenyl)-1H-pyrazol-1-yl]benzenesulfonamide;
4-[3-(4-chlorophenyl)-5-(4-fluorophenyl)-1H-pyrazol-1-yl]benzenesulfonamide;
4-[3-(4-chlorophenyl)-5-(4-methylphenyl)-1H-pyrazol-1-yl]benzenesulfonamide;
4-[3-(4-chlorophenyl)-5-(4-methoxyphenyl)-1H-pyrazol-1-yl]benzenesulfonamide;
4-[3-(4-chlorophenyl)-5-(4-trifluoromethylphenyl)-1H-pyrazol-1-yl]benzenesulfonamide;
4-[3-(4-chlorophenyl)-5-(4-aminophenyl)-1H-pyrazol-1-yl]benzenesulfonamide;
4-[3-(4-chlorophenyl)-5-(4-methoxycarbonylphenyl)-1H-pyrazol-1-yl]benzenesulfonamide;
4-[3-(4-chlorophenyl)-5-(4-nitrophenyl)-1H-pyrazol-1-yl]benzenesulfonamide;
4-[3-(4-chlorophenyl)-5-(4-methylthiophenyl)-1H-pyrazol-1-yl]benzenesulfonamide;
4-[3-(4-chlorophenyl)-5-(4-cyanophenyl)-1H-pyrazol-1-yl]benzenesulfonamide;
4-[3-(4-chlorophenyl)-5-(4-hydroxyphenyl)-1H-pyrazol-1-yl]benzenesulfonamide;
4-[3-(4-chlorophenyl)-5-(4-carboxyphenyl)-1H-pyrazol-1-yl]benzenesulfonamide;
4-[3-(4-chlorophenyl)-5-(4-ethoxycarbonylphenyl)-1H-pyrazol-1-yl]benzenesulfonamide;
4-[3-(4-chlorophenyl)-5-(4-acetamidophenyl)-1H-pyrazol-1-yl]benzenesulfonamide;
4-[3,5-bis(4-chlorophenyl)-4-methyl-1H-pyrazol-1-yl]benzenesulfonamide;
4-[3,5-bis(4-chlorophenyl)-4-(trifluoromethyl)-1H-pyrazol-1-yl]benzenesulfonamide;
4-[3,5-bis(4-chlorophenyl)-4-cyano-1H-pyrazol-1-yl]benzenesulfonamide;
4-[3,5-bis(4-chlorophenyl)-4-(difluoromethyl)-1H-pyrazol-1-yl]benzenesulfonamide;
4-[3,5-bis(4-chlorophenyl)-4-carboxy-1H-pyrazol-1-yl]benzenesulfonamide;
4-[3,5-bis(4-chlorophenyl)-4-(methoxycarbonyl)-1H-pyrazol-1-yl]benzenesulfonamide;
4-[3,5-bis(4-chlorophenyl)-4-amino-1H-pyrazol-1-yl]benzenesulfonamide;
4-[3,5-bis(4-chlorophenyl)-4-acetamido-1H-pyrazol-1-yl]benzenesulfonamide;
4-[3,5-bis(4-chlorophenyl)-4-fluoro-1H-pyrazol-1-yl]benzenesulfonamide; and
4-[3,5-bis(4-chlorophenyl)-4-chloro-1H-pyrazol-1-yl]benzenesulfonamide.

25. The method of claim 17 for use in treatment of inflammation.

26. The method of claim 17 for use in treatment of an inflammation-associated disorder.

27. The method of claim 26 wherein the inflammation-associated disorder is arthritis.

28. The method of claim 26 wherein the inflammation-associated disorder is pain.

29. The method of claim 26 wherein the inflammation-associated disorder is fever.

* * * * *